(12) United States Patent
Pollard

(10) Patent No.: US 8,569,248 B2
(45) Date of Patent: Oct. 29, 2013

(54) CARDIAC GLYCOSIDES TO TREAT CYSTIC FIBROSIS AND OTHER IL-8 DEPENDENT DISORDERS

(76) Inventor: Bette Pollard, Rockville, MD (US)

( * ) Notice: Subject to any disclaimer, the term of this patent is extended or adjusted under 35 U.S.C. 154(b) by 224 days.

(21) Appl. No.: 12/229,399

(22) Filed: Nov. 12, 2009

(65) Prior Publication Data
US 2010/0120704 A1 May 13, 2010

Related U.S. Application Data

(63) Continuation of application No. 10/515,260, filed as application No. PCT/US03/16733 on May 28, 2003, now abandoned.

(60) Provisional application No. 60/383,117, filed on May 28, 2002.

(51) Int. Cl.
| | |
|---|---|
| A61K 31/7048 | (2006.01) |
| A61K 31/585 | (2006.01) |
| C12N 5/00 | (2006.01) |
| A61P 25/28 | (2006.01) |
| A61P 25/16 | (2006.01) |
| A61P 9/00 | (2006.01) |

(52) U.S. Cl.
USPC ............. 514/26; 514/25; 514/175; 435/375

(58) Field of Classification Search
USPC .............. 424/192.1; 435/69.1; 604/892.1
See application file for complete search history.

(56) References Cited

U.S. PATENT DOCUMENTS

| | | | |
|---|---|---|---|
| 3,840,009 A * | 10/1974 | Michaels et al. ............ | 604/892.1 |
| 5,545,623 A | 8/1996 | Matsumori | |
| 6,281,197 B1 | 8/2001 | Florkiewicz | |

FOREIGN PATENT DOCUMENTS

| | | |
|---|---|---|
| JP | H08-099894 | 4/1996 |
| JP | H11-500454 | 8/1997 |
| JP | 2002-536415 | 8/2000 |

OTHER PUBLICATIONS

C F George, "Digitalis intoxication: a new approach to an old problem." Britich Medical Journal 1983:286;1533-1534.*

Hiroaki Seino,"Interleukin-8 May Play a Role in Leukocytosis With Diabetic Ketoacidosis", J. Japan Diab. Soc., 41 (8)699-704, 1998.

Olivier Tabary, "High Suscepibility fo Cystic Fibrosis Human Airway Gland Cells to Produce IL-8 Through the IxB Kinase a Pathway in Response to Extracellular NaCl Content", Journal of Immunology 164:3377-3384, 2000.

David J. McConkey, "Cardiac Glycosides Stimulate Ca2+ Increases and Apoptosis in Androgen-Independent, Metastic Human Prostate Adenocarcinoma Cells", Cancer Research, 60(14) pp. 3807-3812, Jul. 15, 2000.

Judith A. Smith, "Inhibition of export of fibroblast growth factor-2 (FGF-2) from the prostate cancer cell lines PC3 and DU145 by Anvirzel and its cardiac glycoside component, oleandrin", Biochemical Pharmacology, 62(2001) 469-472.

N. G. McElvaney, "Modulation of Airway Inflammation in Cystic Fibrosis", Journal of Clinical Investigation 90(4) pp. 1296-1301, Oct. 1992.

Arlene A. Stecenko, "Dysregulated Cytokine Production in Human Cystic Fibrosis Bronchial Epithelial Cells", Inflammation 25(3) 2001.

* cited by examiner

*Primary Examiner* — Walter Webb
(74) *Attorney, Agent, or Firm* — Dennis H. Lambert

(57) ABSTRACT

A method of inhibiting the secretion of IL-8 and other pro-inflammatory cytokines from cells secreting elevated levels of these compounds is provided. The method includes contacting the cell with a composition comprising a cardiac glycoside such as oleandrin. The cardiac glycoside can be used to treat cystic fibrosis and other IL-8 dependent disorders by lowering levels of spontaneously secreted IL-8 and other pro-inflammatory cytokines. Oleandrin was found to suppress the secretion of IL-8 from cultured CF lung epithelial cells in the nanomolar concentration range. Structure-activity relationships (SARs) for cardiac glycosides are also elucidated.

16 Claims, 5 Drawing Sheets

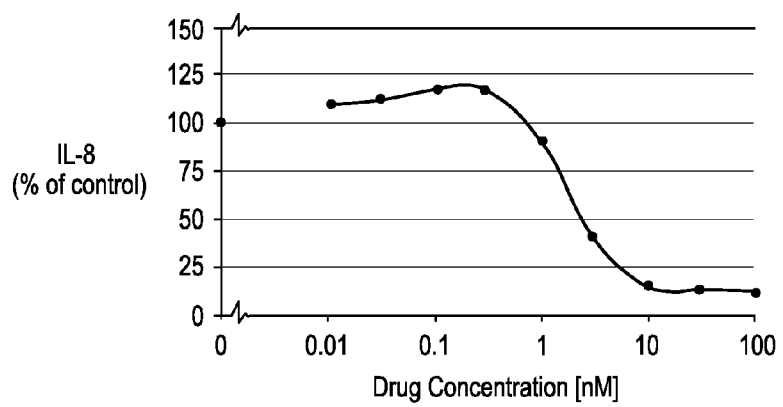
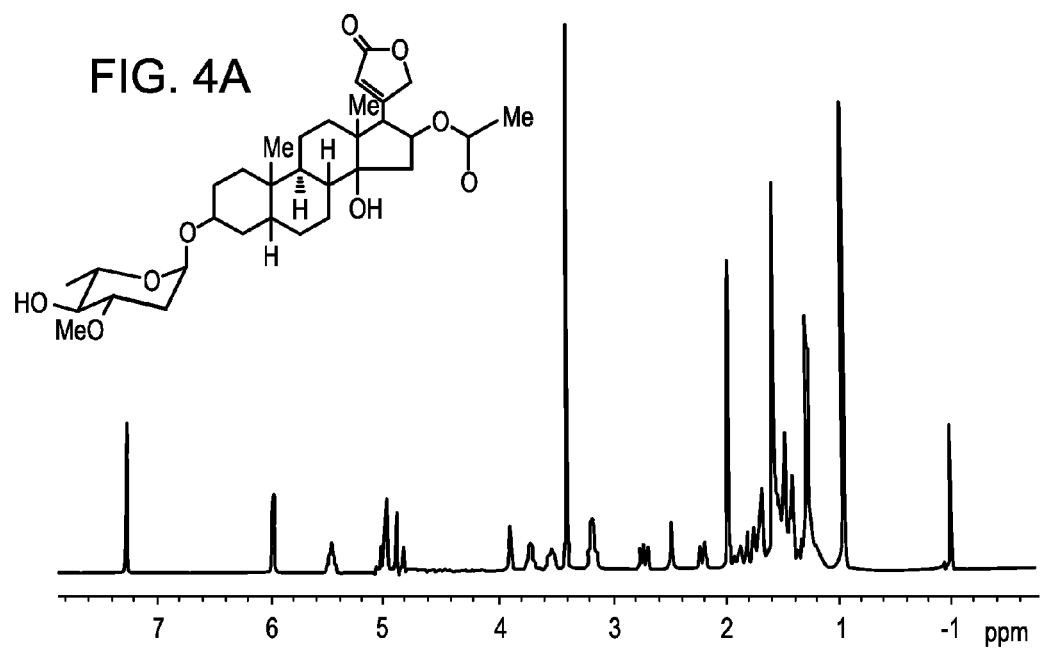

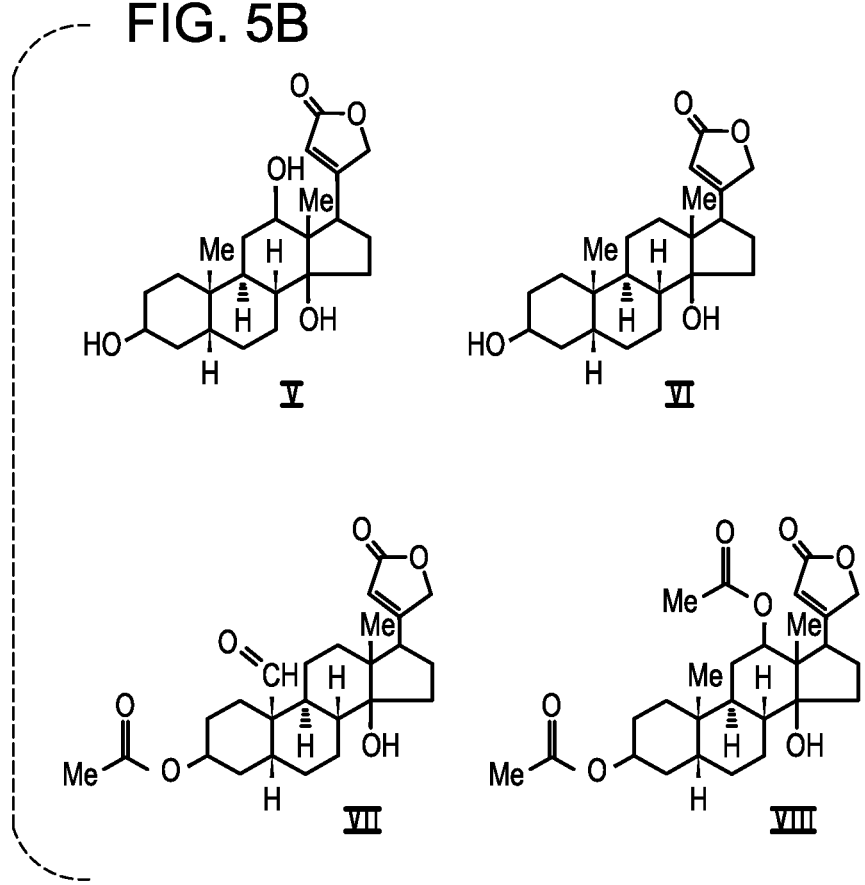

CARDIAC GLYCOSIDES TO TREAT CYSTIC FIBROSIS AND OTHER IL-8 DEPENDENT DISORDERS

This application claims priority as a CONTINUATION of prior application U.S. Ser. No. 10/515,260, filed Aug. 26, 2005 now abandoned, which is a national phase entitled to priority from PCT/US03/16733, filed May 28, 2003, which is entitled to priority from U.S. Provisional Application No. 60/383,117, filed May 28, 2002, the disclosure of each of which priority applications is incorporated herein by reference.

BACKGROUND OF THE INVENTION

1. Field of the Invention

The present invention relates generally to the use of cardiac glycosides such as oleandrin to inhibit the secretion of IL-8 from cells secreting elevated levels of IL-8.

2. Background of the Technology

Cystic fibrosis is the most common autosomal recessive lethal disease in the United States (Welsh, et al. (1995)). Approximately 5% of the population carries one mutant CFTR gene (Rommens, et al. (1989); Riordan, et al. (1989); Kerem, et al. (1989)), and the disease occurs in a frequency of 1 in 2500 live births. Statistically, death occurs in the majority of patients by age 28. At the present time the respiratory difficulties and ensuing complications of inflammation and lung infection are directly responsible for the eventual death of over 90% of CF patents. In control individuals, inflammation is regulated by well-characterized signaling pathways. However, in CF inflammation is out of control, eventually causing destruction of the lung. The consequences are terminal if a lung cannot be found for transplantation.

The CF lung has been described as microscopically normal at birth, with subtle abnormalities in mucus secretion appearing very early (Pilewski, et al. (1999)). Bacterial infection and objective evidence of inflammation occur at later times, with a clear temporal evolution of different principal bacterial pathogens. For example, *Staphylococcus aureus* and *Hemophilus influenzae* take up residence in the CF airway early, the mean age of positive culture being 12.4 months (Abman, et al., 1991). By comparison, *Pseudomonas aeruginosa* infection follows at a substantially later time, the mean age of first positive culture being 20.8 months. Persistent colonization by *P. aeruginosa* characterizes the older CF patient, and profound, persistent cellular evidence of inflammation accompanies persistent infection as the patient approaches the terminal phases of the disease.

As the CF patient ages, the CF lung becomes characterized by elevated levels of white cells. These include polymorphonuclear leukocytes, macrophages, monocytes, lymphocytes and eosinophils. It is hypothesized that these cells are attracted from the circulation into the airway by the high levels of interleukin-8 (IL8) and other pro-inflammatory factors such as IL-1$\beta$, IL-6, leukotriene, B$_4$, RANTES, and TNF$\alpha$. These factors mark the character of the CF lumenal milieu (Bonfield, et al, (1995a); ibid (1995b)). Among these factors, IL-8 ranks as the most prevalent and potent. IL-8 is an 8 kDa chemokine protein which is a principal chemotactic agent for neutrophils and T cells (Cruse, et al. (1995)). This chemokine is of specific importance for cystic fibrosis because it is profoundly elevated in bronchoalveolar lavage fluids, sputum, and serum from CF patients (Dean, et al. (1993); Richman-Eisenstat, et al. (1993); Francoeur, et al. (1995); Armstrong, et al. (1997)). It had been considered possible that high IL-8 levels might be secondary to chronic or persistent infections. However, both IL8 message and protein are elevated in bronchoalveolar lavage fluids from infants with CF as early as 4 weeks of age (Khan, et al. (1995)). Importantly, hypersecretion of IL-8 occurs prior to objective evidence of infection by viruses, fungi or common CF pathogenic bacteria (Khan, et al (1995)). The concept of the generality of a pro-inflammatory state for CF epithelia is further manifest by the fact that fecal. IL-8 levels in CF children are approximately 1000-fold elevated over non-CF controls (Briars, et al. (1995)). Fecal IL-8 levels are correlated with lung function (FEV1, forced expiratory volume in one second), and only to some extent with established *Pseudomonas* infection. A recent study with bronchial biopsies from CF patients undergoing lung transplant has demonstrated consistent up-regulation of IL-8 expression in submucosal gland cells (Tabary, et al. (1998)). Thus, based on these clinical criteria, high IL8 levels would appear to be intrinsic to the CF lung.

Consistently, airway epithelial cells isolated from CF patients secrete more IL-8 than do cells cultured from patients without CF (Bedard, et al. (1993); Ruef et al. (1993); Dimango, et al. (1998)). Interestingly, cells cultured from much higher in the airway, such as those from the nasal epithelium, do not show this disparity between control and CF patients (Black, et al, (1998)). In addition, CF respiratory epithelial cells are hyper-responsive in terms of IL-8 secretion to *Pseudomonas* cells and toxins (Massion, et al. (1994); Dimango, et al. (1998)), or to a combination of TNF$\alpha$ and INF$\gamma$ (Schweibert, et al. (1999)). CFTR levels in human lung are highest in submucosal glands. High levels of IL-8 mRNA and protein have been shown in these tissues from CF patients, both in vitro and in vivo (Tabary, et al. (1998)). In the latter study, other pro-inflammatory cytokines such as IL-1$\beta$ and IL-6 were unaffected by the CF condition. The high levels of IL-8 production by CF epithelial cells have been proposed to be due to retention of mutant CFTR in the endoplasmic reticulum, which, by an unknown mechanism, activates NF$\kappa$B via activation of I$\kappa$B (DiMango, et al. (1998)). Attention is drawn to the NF$\kappa$B system because it is known that transcription of the IL-8 gene is activated in normal epithelial cells when activated NF$\kappa$B migrates from the cytosol to the nucleus and binds to the IL-8 promotor. An adenovirus hyper-expressing IkB$\alpha$ has been employed to suppress IL-8 secretion both from a CF cell line ("CFTE"), as well as from mouse lung (as MIP2), when instilled simultaneously with an infectious dose of *P. aeruginosa* (Griesenbach, et al. (1999); ibid (2000).

It would be desirable to develop compositions that reduce the secretion of IL-8 and other pro-inflammatory cytokines from cells secreting elevated levels of these compounds. These compositions could be useful in the treatment of disease conditions characterized by elevated levels of these compounds.

BRIEF DESCRIPTION OF THE DRAWINGS

The present invention may be better understood by reference to the accompanying drawings in which:

FIG. 3 is a graph showing the effect of oleandrin on IL-8 secretion from cystic fibrosis lung epithelial cell IB-3;

FIG. 4A illustrates the nuclear magnetic resonance (NMR) spectrum of oleandrin used in these experiments;

FIGS. 5A and 5B illustrate the structures of various oleandrin analogues.

SUMMARY OF THE INVENTION

According to a first aspect of the invention, a method of inhibiting the secretion of IL-8 from a cell secreting elevated levels of IL-8 comprising contacting the cell with a composition comprising a cardiac glycoside is provided. According to this aspect of the invention, the cell can be a CF lung epithelial cell. Also according to this aspect of the invention, the cardiac glycoside can be selected from the group consisting of oleandrin, digitoxin, digoxin, ouabain, digoxigenen, digitoxigenen, and acetyl-stropanthidin.

According to a second aspect of the invention, a method of treating disease conditions characterized by elevated levels of IL-8 comprising administering to a mammal suffering from the disease a composition comprising an effective amount of a cardiac glycoside is provided. According to this aspect of the invention, the mammal can be a human. Also according to this aspect of the invention, the elevated levels of IL-8 can result from a condition selected from the group consisting of cardiopulmonary bypass surgery; cardiopulmonary arrest; inflammatory bowel disease; lung disorders and lung conditions; traumatic brain injury; stroke; transplant graft rejection; Alzheimer's disease; Parkinson's disease; HIV; viral infections; and fevers resistant to cyclooxygenase inhibitors.

According to a third aspect of the invention, a method of treating conditions characterized by elevated levels of IL-8 in a human suffering from cystic fibrosis comprising administering to the human an effective amount of a composition comprising a cardiac glycoside is provided.

DETAILED DESCRIPTION OF THE PREFERRED EMBODIMENTS

IL-8 secretion by the CF tracheal epithelial cell line 18-3 is elevated compared to IL-8 secretion by the same cell line corrected with wildtype CFTR (Eidelman, et al. (2001a)). Therefore, elevated levels of IL-8 secretion may be caused by mutant CFTR and a drug or gene able to correct the trafficking defect of ΔF508-CFTR may also lower IL-8 secretion.

The present inventor has found that IL-8 secretion by IB3 cells is suppressed not only by wildtype CFTR but also by CPX and the phospholipid modifying agent MEA (methylethylamine). The present inventor has also found that hypersecretion of IL-8 from CFTE cells is suppressed by CPX. This finding supports the concept that IL-8 secretion is relevant to understanding the pathology of cystic fibrosis from the vantage point of CF epithelial cell dysfunction.

Figure 1:
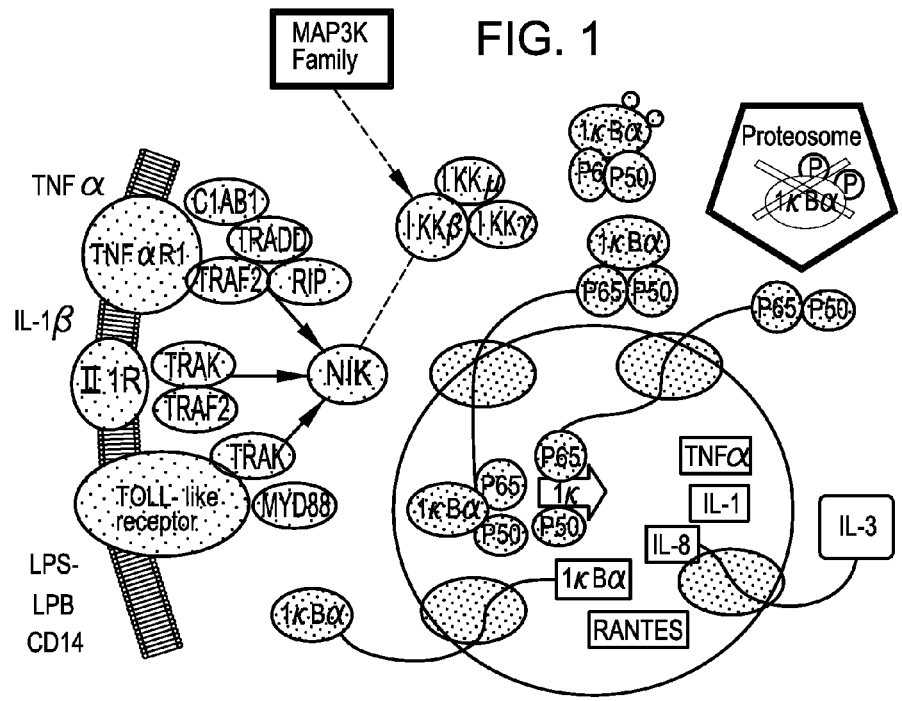
FIG. 1 illustrates the NF$\kappa$B activation pathway leading to synthesis of IL-8.

As set forth above, the NFκB signaling pathway has been implicated in IL-8 expression. However, the number of actual or potential components in this pathway is enormous. As shown in FIG. 1, initially independent pathways involving TNFα, IL-1 and bacterial lipopolysaccharides (LPS) are hypothesized to converge on NIK, or on members of the MAP6K family, which then activate a complex of IκB kinases (IKKα, β, and γ). The NFκB complex, composed of p65 and p50 components, sits inactive when complexed with IκB. However, when the activated IKK's phosphorylate IκB, the proteosome attacks the phospho-IκB, releasing the residual p65/p50 complex. This NFκB heterodimer enters the nucleus and binds to κB sites on promotors for IL-8, IκB, TNFα, IL-1, and several other inflammatory signaling molecules. In this manner IL-8 gets transcribed and eventually secreted. Once within the nucleus, the NFκB complex is removed from the κB sites by a fresh IκB molecule from the cytosol, which then leaves the nucleus as an p65/p50/IκB complex, ready for future activation.

As can be seen from FIG. 1, the p50 component is synthesized as a larger p105 precursor, which is able to bind to p65. When bound to p65, p105 acts not only as a p50 ligand to p65, but also as an inhibitory IκB-like ligand. In this latter role, the IKK's have no activating effect on the NFκB complex.

As further illustrated in FIG. 1, the TNFαR1 receptor transduces the TNFα signal to the IκB kinase system through a complex of gene products including TRADD (TNF Receptor-1 Associated Death Domain protein), TRAF2 (TNF Receptor Associated Factor), RIP (TNF Receptor Interacting Protein), and CIAP1/2 (Inhibitor of Apotosis Protein 1). As the names imply, this system is closely connected to regulation not only of inflammation but also the apoptotic pathway. For example, the TRADD adapter also transduces interactions between TNFαR and downstream apoptotic components such as caspase 7, FLICE, FAS antigen, FAN, and TRAMP (not shown). In the context of the simple "divide-or-die" alternatives available to cells, this cluster of TNF-associated gene products is thought to be initially used by cells for both purposes. However, it is important to appreciate that in the case of CF cells, the potential for cross-talk between pro-inflammatory and pro-apoptotic pathways may be more than idle speculation. For example, a 10-fold elevation in TUNEL labeling for fragmented DNA has been reported in crypt enterocytes observed in duodenal biopsies of CF patients (Maiuri, et al. (1997)). In addition, FAS and FAS ligand expression, markers of apoptosis, are markedly increased over non-CF controls in biopsies of CF broncheal epithelium and cultured CF tracheal cell lines (Durieu, et al. (1999)). Disordered regulation of apoptosis has also been observed in heterologous C127 cells expressing ΔF508-CFTR (Gottlieb, et al. (1996)).

Figure 2:
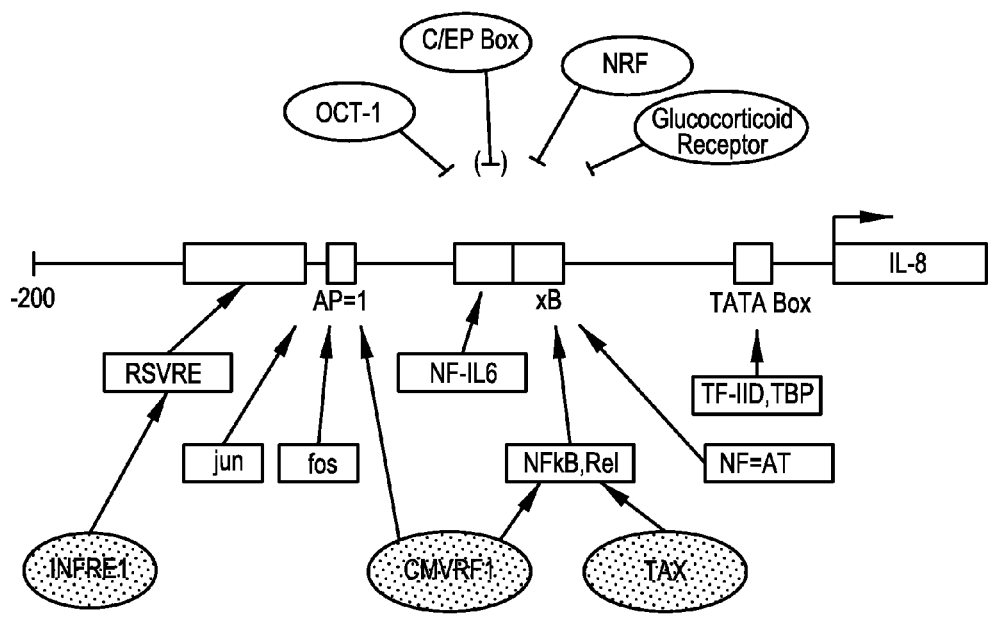
FIG. 2 illustrates the Activation of IL-8 promoter by NFkB and other cis acting transcription factors.

The sequence of known cis-acting elements in the IL-8 promoter is summarized in FIG. 2. Some of these elements are responsive to intrinsic regulators such as NFκB and AP-1, while others are pathogen-specific. It is therefore possible that certain combinations of these factors may be responsible for the high intrinsic levels of IL-8 expression and secretion in CF cells. In addition, they may also be responsible for the suppression of the baseline levels of IL-8 secretion in the presence of wildtype CFTR or CPX, as well as for the physiological response to P. aeruginosa. We summarize the identities of the experimentally validated cis-acting elements, as follows: (i) RSVRE, (binding site: −162 to −132) is the newly discovered Respiratory Syncytial Virus Responsive Element, which is responsible for the intense IL-8-dependent pulmonary inflammation in RSV infection (Casola et al (2000)); (ii) IFNRF1, the Interferon Regulating Factor 1, binds to and further activates the RSVRE (Casola, et al. (2000)); (iii) AP-1, (binding site: −126 to −120), is activated by the heterodimer of JunD/cFos, and is superactivated in cytomegalic virus (CMV) infection by the (iv) CMVRE1 (CMV Responsive Element); (v) NF-IL6 (binding site: −94 to −81) is an activator of IL-8 transcription and is a possible overlapping site of interaction with C/EBPα (CCAAT box enhancer binding protein α); (vi) NFκB (binding site: −80 to −70) is activated by the family of NF B/Rel transcription factors, and super-activated by CMV1E1; (vii) C/EBPα (binding site: −91 to −81) partially overlaps the NFκB site, and either activates or inhibits IL-8 transcription depending on the context (Victor, et al. (1996); Stein, et al. (1993)); (viii) GC (glucocorticoid receptor) binds to NFκB and inhibits transcription (summarized in Baldwin (1996)); (ix) OCT-1 is a homeo-domain factor that suppresses IL-8 transcription by acting on NF-IL6

(Wu, et al. (1997)); (x) NF-AT (Nuclear Factor of Activated T cells) binds at or near the NFκB site and activates transcription (Roebuck (1999)); (xi) TAX, coded by HTLV-1, binds to NFκB and promotes transcription (Suzuki, et al. (1994)); (xii) NRF (binding site: partial overlap with NFκB) is the NFκB Repressing Factor which is principally responsible for basal silencing, but is also required for full IL-8 mRNA production (Nourbakhsh, et al. (2000)); and (xiii) TATA box (binding site: −20 to −13) binds TF-IID and the TBP, and is considered necessary for IL-8 transcription. In silico algorithms predict many more potential sites, but only the ones described above have been experimentally validated.

Oleandrin, with the structure of 16β-(acetyloxy)-3β-[2,6-dideoxy-3-O-methyl-L-arabino-hexopyranosyl)oxy]-14 hydroxycard-2O-(22)enolide (Merck Index #6786, 11th Edition, 1989), is a cardiac glycoside derived from the botanical source Nerium Oleander, Linné, commonly known as Oleander or Laurier rose. The oleander is known as a poisonous plant, and oleandrin, and related compounds such as oleandrogenin, and others, are responsible for the toxicity of the entire plant (Kingsbury (1964)). According to the Merck Index, the LD50 for intravenous administration to the cat is 0.3 mg/kg. LD-50 stands for dose that is lethal to 50% of, in this case, cats. Assuming the body weight is all water and that the distribution is uniform, this corresponds to a concentration of 0.6 µM. Since these assumptions minimize the apparent concentration, the LD-50 is probably higher. The mechanism of death is cardiotoxicity due to cardiacglycoside structure and properties of oleandrin. A hot-water extract of oleander leaves, a sort of oleander "tea", is sold under the trade name Anvirzel™ by Salud Integral (Sanitary Registration Number M-07708), Republic of Honduras, for "treatment of cancer, AIDS, hepatitis C, as well as other diseases related to the immune system." The composition of a vial of 10 ml volume contains 150 mg of Nerium oleander extract. The details of the extract are not specified in the Sanitary Registration Certificate, but it probably contains many components, mostly unknown (http://www.saludintegral/hn/company_health_registration.htm). Manna, et al. (2000) have reported that oleandrin, at 1 µM concentration, suppresses tumor necrosis factor (TNFα)-dependent activation of NFκB in a variety of cultured cancer cells by acting in the vicinity of the NFκB-inducing kinase (NIK). However, the tumor cells do not die.

In addition to cystic fibrosis, IL-8 is thought to play a role in other disease states and conditions. For example, cardiopulmonary bypass operations are associated with a transient rise in circulating IL-8 and other cytokines (Nandate, et al. (1999)). Brain dysfunction following the operation occurs in a portion of the patients, and the mechanism may involve activation of inflammatory processes in the brain. In support of this hypothesis, Nandate, et al. (1999) show that during and following the bypass operation, IL-8 levels are consistently higher in the jugular bulb, containing blood coming from the brain to the heart, than in the paired arterial samples. Thus, specific and significant IL-8 production could be found to be produced in the cerebrovascular bed during and following the operation. The authors also report that at least one intervention, hypothermia, suppresses the changes. Thus, drugs that interfere with IL-8 production should be useful in ameliorating morbidity and mortality associated with cardiopulmonary bypass operations.

Drabe, et al. (2001) have pursued genetic components associated with increased IL-8 production during cardiopulmonary bypass operations. The apolipoprotein E4 allele is historically associated with increased propensity to atherosclerosis, higher levels of lipoprotein (a), and early Alzheimers Disease. Drabe, et al. (2001) show that patients carrying the apolipoprotein E4 allele have higher baseline levels of IL-8 and TNFα than patients lacking this alleles. Following cardiopulmonary bypass, the apolipoprotein E4 patients, comprising 27% of the patient cohort, also have increased release of both IL-8 and TNFα, compared to patients lacking this allele. It is therefore suggested that patients with the E4 genotype should have additional perioperative therapy for the aberrantly increased systemic inflammatory response. Thus drugs that interfere with IL-8 production should thus be useful in ameliorating morbidity and mortality associated with cardiopulmonary bypass operations.

Patients arriving in the hospital emergency room after suffering cardiopulmonary arrest (CPA) also have increased levels of serum IL-8 and TNFα. These levels peak within 12 hours post-admission, or within 6 hours after return of spontaneous circulation (ROSC; Ito et al. (2001). Ito, et al. (2001) also report that serum IL-8 levels in those patients with significantly higher levels of IL-8 tend to die or become brain dead within one week of return of spontaneous circulation. Excessive administration of epinephrine is also associated with significantly elevated of IL-8 following return of spontaneous circulation. The source of the IL-8 in the serum is not specified. However, considering the data of Nandate, et al. (1999), a central origin could be suspected. Whatever the source, it is likely that drugs that interfere with IL-8 production following ROSC might be useful in ameliorating morbidity and mortality associated with cardiopulmonary arrest.

IL-8 and other chemokines have also been implicated in the pathogenesis of inflammatory bowel disease (Imada, et al. (2001)). The levels of IL-8 are especially elevated in acute organ cultures of patients with active ulcerative colitis. Imada, et al. (2001) show that increased expression of IL-8 message can be detected in macrophages, pericrypt myofibroblasts, and epithelium. Dietary fat has been proposed to exacerbate intestinal inflammation, and studies with monolayers of colon epithelial cells indicate that medium-chain fatty acids such as oleic acid cause a five-fold elevation of IL-8 secretion (Tanaka, et al. (2001)). The process follows the anatomy of digestion, since the fatty acid is added on the apical (lumenal) side, while IL-8 secretion occurs in the basolateral (serosal) direction. Thus drugs that interfere with IL-8 production should be useful in the treatment of inflammatory bowel disease.

Inflammation processes are historically associated with the pathogenesis of atherosclerosis, and high levels of IL-8 have been found in atheromatous plaques (Wang et al. (1996)). Among the mechanisms, high IL-8 has been directly implicated, and the processes regulating IL-8 synthesis can be studied in vitro in cultures of human aortic endothelial cells. IL-8 is synthesized in these cells via multiple convergent pathways (Takata, et al. (2001)). For example, prevastatin (an inhibitor of 1,3-hydroxy-3-methylglutaryl co-enzyme A reductase) not only lowers cholesterol, but also suppresses thrombin-induced IL-8 production in these cells cultured in high glucose medium. The effect is not on baseline IL-8 levels, which are such a problem in cystic fibrosis, but on stimulated levels induced by thrombin. The mechanism involves inhibition of the thrombin-induced transition of ras from the cytosol to the plasma membrane. The consequence is suppression of activation of the ras-MAP(p44/42) kinase pathway, but not the kinase itself. Thus drugs that specifically target IL-8 production should be useful in treating inflammatory aspects of atherosclerosis.

While IL-8 levels in CF lungs are tonically elevated over controls by factors of 1000 fold or more, much more modest levels of IL-8 elevation, in the range of 2-10 fold, have been noted in some other pulmonary diseases and disorders. Modest but significant elevations of IL-8 have been reported in noneosinophilic asthma (Gibson, et al. (2001)). IL-8 levels in asthmatic children are detectable, and are correlated with symptoms (Marguet, et al. (2001)). Somewhat elevated IL-8 levels have been found in asymptomatic nonspecific airway hyperresponsiveness (BHR; Betz, et al. (2001)). Patients with chronic obstructive pulmonary disease (COPD), sometimes used as a theoretical control for cystic fibrosis, also have high levels of IL-8 (Betz, et al. (2001)). The two problems are thought to be temporally related because it is thought that asymptomatic BHR can progress to COPD. From an acute point of view, multi-trauma patients often develop nosocomial pneumonia (NP), and a higher level of IL-8 in bronchoalveolar lavage fluids of the incoming patient is predictive of the development of NP (Muehlstedt, et al. (2001)). For these reasons, drugs that specifically target IL-8 production should be useful in treating or preventing asthma, BHR COPD, and NP.

Thermal injuries (viz., burns) are closely associated with increases in cytokines such as TNF, IL-6 and IL-8 in the systemic circulation, normal and thermally injured skin and lung (Rodriguez, et al. (1993); Vindenes, et al. (1995)). The lung cytokine response to acute thermal injury is thought to be responsible for initiating local organ failure. The highest levels of IL-8 are associated with septic patients who died (Yeh, et al. (1997)). High IL-8 levels are also associated with delayed healing of thermal wounds, by mechanisms involving suppression of fibroblast replication and inhibition of myosin ATPase (Iocono, et al. (2000)). Thus suppression of IL-8 production in burn patients might be expected to make a therapeutic contribution.

Acute pancreatitis in humans is often associated with multi-organ dysfunction syndrome (MODS), principally affecting the lung (Bhatia, et al. (2001)). Faithful experimental acute pancreatitis models have been studied in rabbits, in which IL-8 is elevated in serum and lung, and acute lung injury observed (Osman, et al. (1998); Osman, et al. (1999)). Infusion of an antibody against IL-8 during the acute pancreatitis challenge prevents lung damage, as evidenced by reduced neutrophil infiltration in the lung, while pancreatic necrosis and systemic release of pancreatic enzymes is unaffected (Osman, et al. (1998)). Thus suppression of IL-8 production during acute pancreatitis may useful in suppressing MODS, with special emphasis on the lung.

Smoke inhalation, as found in victims of fires or injured firemen, causes lung endothelial injury and formation of pulmonary edema. Laffon, et al. (1999) have developed a rabbit model in which cooled smoke causes significant increases in alveolar epithelial permeability and a significant reduction in bidirectional transport of protein across the pulmonary epithelium. However, Laffon, et al, (1999) show that administration of an anti-IL-8 antibody restores alveolar epithelial permeability to normal levels and significantly increases bidirectional transport of protein. Thus increased IL-8 is an important mediator of lung injury following smoke inhalation, and drugs capable of suppressing IL-8 should be useful therapeutics for smoke inhalation problems affecting lung function.

Acid injury to the lung is associated with an increase in alveolar epithelial permeability to protein and a reduction in net alveolar fluid clearance (Modelska, et al. (1999)). However, pretreatment with an anti-IL-8 antibody significantly reduces the acid mediated increase in bi-directional transport of protein across the alveolar epithelium, and restores alveolar fluid clearance to normal (Modelska, et al. (1999)). Thus drugs capable of suppressing IL-8 should be useful therapeutics for acid injury to the lung.

Reexpansion pulmonary edema (REPE) often follows reexpansion of a collapsed lung due to a mechanism of increased microvascular permeability and inflammatory cell accumulation (Nakamura, et al. (2000)). Local overproduction of IL-8 is responsible for the process. Pretreatment with anti-IL-8 antibody significantly reduces the neutrophil count in bronchoalveolar lavage (BAL) fluid and suppresses REPE. Thus drugs capable of suppressing IL-8 should be useful therapeutics for reexpansion pulmonary edema in the lung.

Following traumatic brain injury, increases occur in the levels of IL-8 and other proinflammatory cytokines (Ott, et al. (1994)). In children with severe head injuries there is a significant association between survival after traumatic brain injury and levels of IL-8 in the cerebrospinal fluid (CSF) (Whalen, et al. (2000); see also Sherwood, et al. (2000)). As summarized by Ott, et al. (1994), IL-8 and related agents play a central role in the cellular cascade of injury, both centrally and peripherally by inducing fever, neutrophilia, muscle breakdown, alternd amino acid metabolism, depression of serum zinc levels, production of hepatic acute phase reactants, increased endothelial permeability and expression of endothelial adhesion molecules. Ott, et al. (1994) also emphasize that specific failures of gut, liver and lung have been identified due to IL-8 and other brain-derived cytokines such as IL-1, IL-6, and TNFα. Kossmann, et al. (1997) and Maier, et al. (2001) have validated the brain origin of circulating IL-8, as well as IL-1 and IL-6. They demonstrate that following brain trauma these interleukins are higher in cerebrospinal fluid (CSF) than plasma. Maximal values in IL-8 in CSF are also associated with destruction of the blood brain barrier (Kossmann, et al. (1997); Maier, et al. (2001)). While there appears to be a role for IL-8 in stimulating repair in the brain by the NGF pathway (Kossmann, et al. (1997); Sherwood, et al. (2000)), the massively elevated IL-8 levels seen in traumatic brain injury appear to exert a strong, contrary pathophysiological connection to adverse consequences of traumatic brain injury. We therefore interpret these data to suggest that drugs capable of suppressing production of IL-8 should be useful in reducing morbidity and mortality following traumatic brain injury, thereby permitting the occurrence of any positive reparative actions of low levels of IL-8.

Stroke, a localized ischemic trauma to the brain, significantly increases levels of IL-8 and other related factors in the cerebrospinal fluid (CSF). IL-8 levels increase immediately following stroke, and peak on day 2 (Tarkowski, et al. (1997)). Higher levels of IL-8 in the CSF are observed following white matter strokes than grey matter strokes. Kostulas, et al. (1999) report that following stroke, IL-8 mRNA levels in perpheral blood neutrophils remain increased for up to 30 days following stroke, while other cytokines return to normal. In animal models of stroke, intracysternal administration of blocking antibodies to IL-8 are found to prevent cerebral reperfusion injury, and endotoxemia-induced acute respiratory distress syndrome-(ARDS)-like lung injury (Matsumoto, et al. (1997a); Mukaida, et al. (1998)). An intracysternal neutralizing IL-8 antibody has also been reported to reduce brain edema and infarct size in rabbit brain following experimental transient focal ischemia (Matsumoto, et al. (1997b)). We interpret these data to indicate that drugs with antibody-like capacities to lower brain levels of IL-8 might be useful in the treatment and possible prevention of stroke.

Diabetes, affecting 7% of the population, is associated with an approximately 4-fold elevation in ambient serum IL-8 (Zozulinska, et al. (1999)). The increment is valid for both Type I and Type II diabetics, and is significantly correlated with levels of glycosylated hemoglobin (HbA$_c$). The study was performed in a set of diabetic patients with no evidence of acute or chronic infection, renal failure or ketoacidosis, and a set of age-matched controls. Supportive data have been reported by Yuuki, et al. (2001). The IL-8 signal is a strong beacon for polymorphonuclear leukocytes, and the relationship is consistent with a pro-inflammatory phenotype for diabetes. It is thus likely that drugs that suppress baseline levels of IL-8 should be useful for the treatment of complications of diabetes.

One of the major complications in diabetes is vascular damage in the retina due to high glucose. Indeed, proliferative diabetic retinopathy (PDR) is the most common cause of blindness in the US and Western European populations. Elner et al. (1995), report that significantly higher levels of IL-8 occur in the vitreous humor of diabetes patients with PDR. In contrast, IL-8 levels in vitreous of non-diabetic patients with proliferative vitreoretinopathy, an analogous syndrome not associated with diabetes, are equivalent to control levels found in normal eyes. In addition, other conditions such as idiopathic macular holes, idiopathic macular puckers, vitreous hemorrhages, or uncomplicated retinal detachments have a phenotype of normal IL-8 levels in the vitreous. Yuuki, et al. (2001) also report that levels of IL-8 in vitreous fluids are greater in proliferative diabetic retinopathy (PDR) than in non-inflammatory retinopathy.

In a more recent study, Elner, et al. (1998) report that elevated IL-8 levels can be found only in active cases of PDR, but not inactive PDR cases. Temaru, et al. (1997) show that high glucose concentrations induce elevated IL-8 mRNA expression in cultured human aortic endothelial cells, but not smooth muscle cells. These data are interpreted to suggest that diabetic macroangiopathy is caused by a glucose-dependent gradient of IL-8 between the smooth muscle and the arterial intima. Elner, et al. (1995 & 1998) interpret the data to suggest that IL-8 participates in the pathogenesis of proliferative diabetic retinopathy. For these reasons, drugs that specifically suppress IL-8 production should be useful in treating diabetic complications such as diabetic retinopathy.

Successful transplant surgery of kidneys, lungs and other organs depends upon high quality donor organs that tend not to be rejected by the recipient. Inflammation in the donor organ, as evidenced by high IL-8 levels, is associated with increased likelihood of graft rejection by the recipient (Zivna, et al. (1999)). These authors report that increased serum and urine IL-8 concentrations in recipients 24 hours after kidney transplant is predictive of future rejection episodes. In the case of lung transplants, an increased level of IL-8 in the donor broncho-alveolar lavage (BAL) fluid is associated with severe early graft dysfunction and early recipient mortality (Fisher, et al. (2001)). Fisher, et al. (2001) suggest that severe trauma patients, the frequent source of lungs for transplant, often have increased levels of IL-8, as well as neutrophils that are attracted by IL-8. Stangl et al. (2001) show that IL-8 levels are 10-fold lower in unrelated living renal transplants compared to cadaver kidneys. They conclude that this is the reason for superior long term results from the living renal transplants. These data suggest that drugs or conditions capable of lowering intrinsic production of IL-8 by transplant grafts, whether by treatment of the organ itself or by treatment of the recipient, should reduce the incidence of rejection and recipient death.

Alzheimer's Disease, affecting an ever increasing fraction of the aging population, is believed to be due to toxic effects of brain-derived amyloid beta peptide (AβP). The pathological basis of AβP action on neurons is the increase in intracellular Ca$^{2+}$ via calcium channels formed by the AβP itself (Arispe, et al. (1993); (1996)). Among the consequences of this action are increases in immune/inflammatory pathways associated with IL-8 in affected areas of the brain (Gitter, et al. (1995)). Such affected areas include cortex and hippocampus). Gitter, et al. (1995) show that AβP stimulates IL-8 secretion from human astrocytoma cells. In addition, IL1b potentiates AβP action on IL-8 secretion by astrocytes by 10-fold, a process which is altogether blocked by calcium chelators such as EGTA. The immediate target of the secreted IL-8 may be IL-8 receptors, which are plentiful in the central nervous system. Xia et al (1997) report that IL-8RB colocalizes with AβP-positive neurites in Alzheimer Disease brain, but not with paired helical filaments (PHF) or hyperphosphorylated tau (AT8). Thus while IL-8 may be important in normal brain for signaling between neurons and glia, the action in Alzheimer Disease brain may be to potentiate immune destruction of neurons. These data suggest that drugs that are able to interfere with IL-8 secretion in brain should be useful as therapeutics for Alzheimer Disease.

Parkinson's Disease, caused by destruction of the substantia nigra pars compacta in the midbrain, joins Alzheimer's Disease as one of the neurodegenerative disorders whose incidence is increasingly manifest in the aging population. Polymorphisms of genes associated with the proinflammatory TNFα pathway have been discovered and interpreted as indicating a immunomodulatory effect on sporadic Parkinson's Disease (Kruger, et al. (2000); Nishimura, et al. (2001)). Nishimura, et al. (2000) suggest that TNFα may have a toxic effect on Parkinson's Disease, implying action at the level of the substantia nigra in the brain. MPTP (N-methyl-1-4 phenyl-1,2,3,6-tetrahydropyridine) is a neurotoxin which causes Parkinson's Disease-like syndrome in organisms as phylogenetically diverse as goldfish and man (Pollard, et al. (1992); Gaping, et al. (1995)). Genes associated with inflammatory pathways have been shown to be induced in mouse brain by MPTP (Grunblatt, et al. (2001); Mandel, et al. (2000)). While no specific demonstration of IL-8 on the Parkinson's Disease process has yet been reported, the TNFa pathway terminates at the IL-8 promoter as shown in FIG. 2. Drugs suppressing IL-8 secretion should therefore be useful in treating Parkinson's Disease.

HIV-1 infection of macrophages results in elevation of Interleukin-8 synthesis and secretion of IL-8 by the infected cells. Conversely, IL-8 itself stimulates HIV-1 replication in macrophages and T-lymphocytes (Lane, et al. (2001)). Consistently, Lane, et al. (2001) show that increased levels of IL-8 are present in the lymphoid tissue of patients with AIDS. Furthermore, compounds which block IL-8 receptors also inhibit HIV-1 replication in both T lymphocytes and macrophages. Thus, drugs that are able to interfere with IL-8 secretion might be useful as therapeutics for HIV-1 infection, and AIDS.

HIV-1 infected patients often develop neurological disorders and HIV-1-associated dementia following invasion of the brain by activated T cells and infected macrophages. Kutsch et al. (2000) show that the HIV-1 Tat (72aa) peptide potently induces IL-8 and related cytokines in astrocytes. IL-8 message is seen within an hour, and IL-8 protein is produced. Given the fact that IL-8 potyentiates HIV-1 infection, it follows that drugs that are able to interfere with IL-8 secretion might be useful in preventing or suppressing HIV-1 infections in the CNS leading to HIV-1-associated dementia.

Other viral agents have an impact, either directly or indirectly, on IL-8 production by target cells. In the case of adenovirus (Gilmour, et al. (2001)), the adenoviral gene product E1A primes alveolar epithelial cells to produce elevated levels of IL-8 when exposed to environmental particulate matter that is less than 10 microns in diameter [e.g., PM(10) or hydrogen peroxide ($H_2O_2$)]. In the case of the human rhinovirus (HRV-14; Subauste, et al. (2001)), the growth factors TNFa and EGF induced the cells to both synthesize increased levels of IL-8 and to support increased viral replication in a line of human bronchial epithelial cells. In the case of respiratory syncytial virus (RSV), there is a well known responsive element for RSV on the IL-8 promoter (viz, the RSVRE) which supports a vastly increased level of IL-8 production upon RSV infection. The viral literature is extensive on this point, and so we can only conclude that drugs able to interfere with production of IL-8 during viral infection should have the capacity either to interfere with some viral infections, or to suppress associated inflammatory symptoms.

The rationale for IL-8 suppression of the growth of some tumor cells is not yet apparent. However, adenoviral gene therapy with antisense to IL-8 has been successful in reducing growth of human bladder tumor cells growing subcutaneously in the nude mouse (Inoue, et al. (2001)). The injections of the adenoviral construct were directly into the body of the tumor, and only resulted in inhibition of growth rate relative to control capacity. We can only conclude that drugs able to interfere with production of IL-8 could have the capacity either to interfere with tumor growth, development or metastases.

Certain fevers are known to be resistant to cyclooxygenase inhibitors, and a type of fever caused by intracerebrovascular injection of IL-8 falls into this category (Zampronio, et al. (1994)). These data suggest that drugs able to interfere with IL-8 secretion in brain should be useful as antipyretics for fevers resistant to cyclooxygenase inhibitors.

Psoriasis is an disabling, proliferative skin disorder associated with systemic elevation of lymphocytes (Hoxtermann, et al. (1998)) and other evidences of aberrant cytokine production (Stoof, et al. (2001)). Stoof, et al. (2001)), in a study of the mechanism of action of the antipsoriatic drug dimethylfumarate (DMF), show that DMF, in the range of 5-50 suppresses interferon-gamma-stimulated production of IL-8 and related cytokines by human karatinocytes. These cytokines are thought to be responsible for the perpetuation of psoriatic lesions. The mechanism of action of DMF on IL-8 production may be via the NFκB pathway, since DMF causes nuclear accumulation of cytokine-induced NFκB1/p50 in human dermal fibroblast cells (Vandermeeren, et al., 2001). These data suggest that drugs able to interfere with IL-8 secretion in dermal cells should be useful as anti-psoriatic agents.

Rheumatoid arthritis, afflicting approximately 1% of the population, is a chronic multisystem disease of unknown cause, characterized by persistent inflammatory synovitis, principally in symmetrical peripheral joints (Lipsky (2001)). High basal levels of IL-8 are found in synovial fluid and in synovial cells (Troughton, et al. (1996); Rothe, et al. (1998); Rodenburg, et al. (1999); Olszewski, et al. (2001); Nanki, et al, (2001); Hayashida, et al. (2001)). It has been proposed that IL-8 participates in synovial lesions at the earliest stages of rheumatoid disease (Takahashi, et al. (1999)), and that symptoms coincide with increased synthesis of IL-8 (Kraan, et al, (2001)). The synthesis of IL-8 by synovial attracts ingress of peripheral monocytes (Hayashida, et al. (2001)), as well as angiogenesis, possibly to support the chromic inflammatory state (Koch, et al. (2001)). The mechanism of IL-8 synthesis by synovial cells involves the NFκB pathway (Morel, et al. (2001)) and increases in IL-8 mRNA. Certain other categories of arthritis are also characterized by high levels of IL-8, including Behcet's (Ertenli, et al. (2001)), psoriatic (Konig, et al. (1997)), and Sjogren's (Amin, et al. (2001)). Therapy of rheumatoid arthritis by either methotrexate (Gao, et al. (1998)) or aurothioglucose (Yoshida, et al. (1999)) results in reduction of IL-8 levels in the affected joints. These data suggest that drugs able to interfere with IL-8 secretion in synovial tissues should be useful for treatment of rheumatoid and other types of IL-8 related arthritis.

As described above, cystic fibrosis is characterized by a high level of spontaneous, baseline IL-8 secretion. The mechanism of this high baseline secretion is not known, but may be associated with upregulation of a set of genes associated with the TNFαR/NFκB pathway (Eidelman, et al. (2001a)). It was therefore hypothesized that if oleandrin could suppress TNFα-activated activation of NFκB in tumor cells, it might also suppress the high baseline levels of IL-8 in Cystic Fibrosis (CF) cells. To test this hypothesis, the CF lung epithelial cell line IB-3 was exposed to different concentrations of oleandrin over a 48 hour incubation period.

Figure 4B:
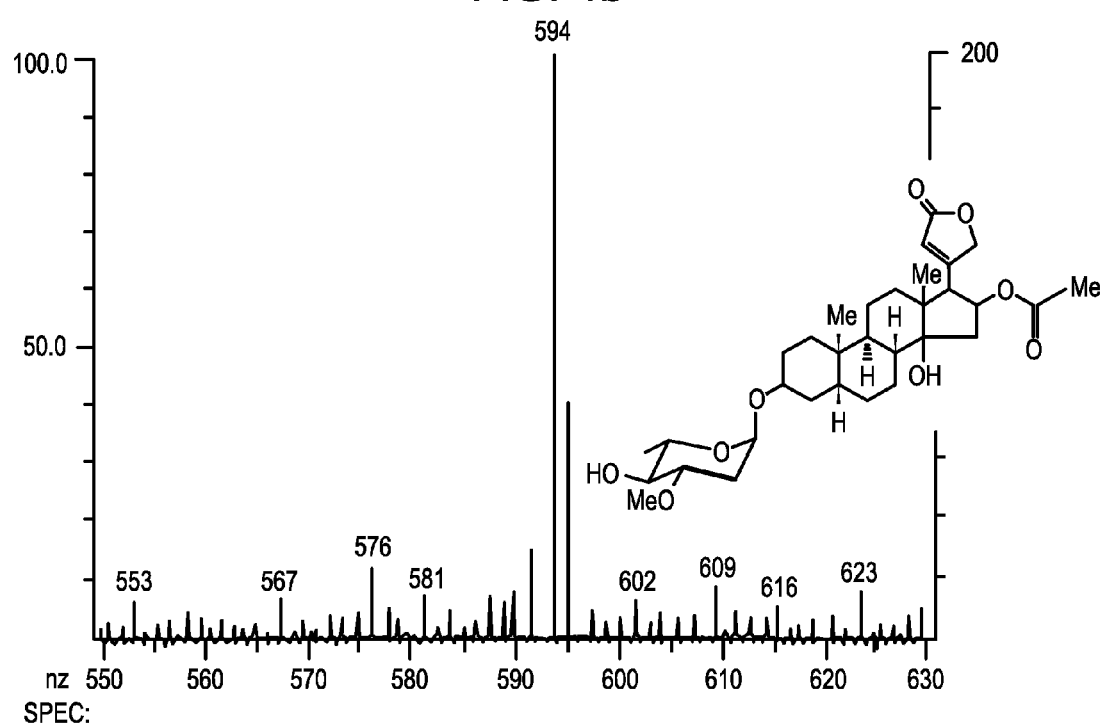
FIG. 4B illustrates the mass spectrum of oleandrin used in these experiments.

The data are shown in FIG. 3, where the titration shows an ID50 (dose for 50% inhibition) for spontaneous IL-8 secretion of approximately 1 nM. Oleandrin was obtained from Indofine Chemicals. The ID50 for oleandrin is approximately 1 nM. The data plotted in FIG. 3 are the average of 3 separate experiments. The assay is performed exactly as described in Eidelman et al. (2001a), except that the compound to be tested is oleandrin, and the ethanol concentration is 0.001%. The purity of oleandrin was confirmed by NMR and Mass Spectroscopy. FIGS. 4A and 4B show plots generated for the oleandrin used in these experiments by NMR and Mass Spectroscopy, respectively.

Experiments were also conducted to determine the structure-activity-relationship (SAR) for oleandrin suppression of IL-8 secretion from CF lung epithelial cell. Oleandrin and related cardiac glycosides are characterized by a cholesterol nucleus, the possible attachment of sugars at the 3-OH position, and various chiral substitutions throughout the structure. Experiments were conducted to elucidate the structure-activity-relation (SAR) by testing the potency of various modified versions of oleandrin. In this manner, the pharmacophor can be specified.

Figure 5A:
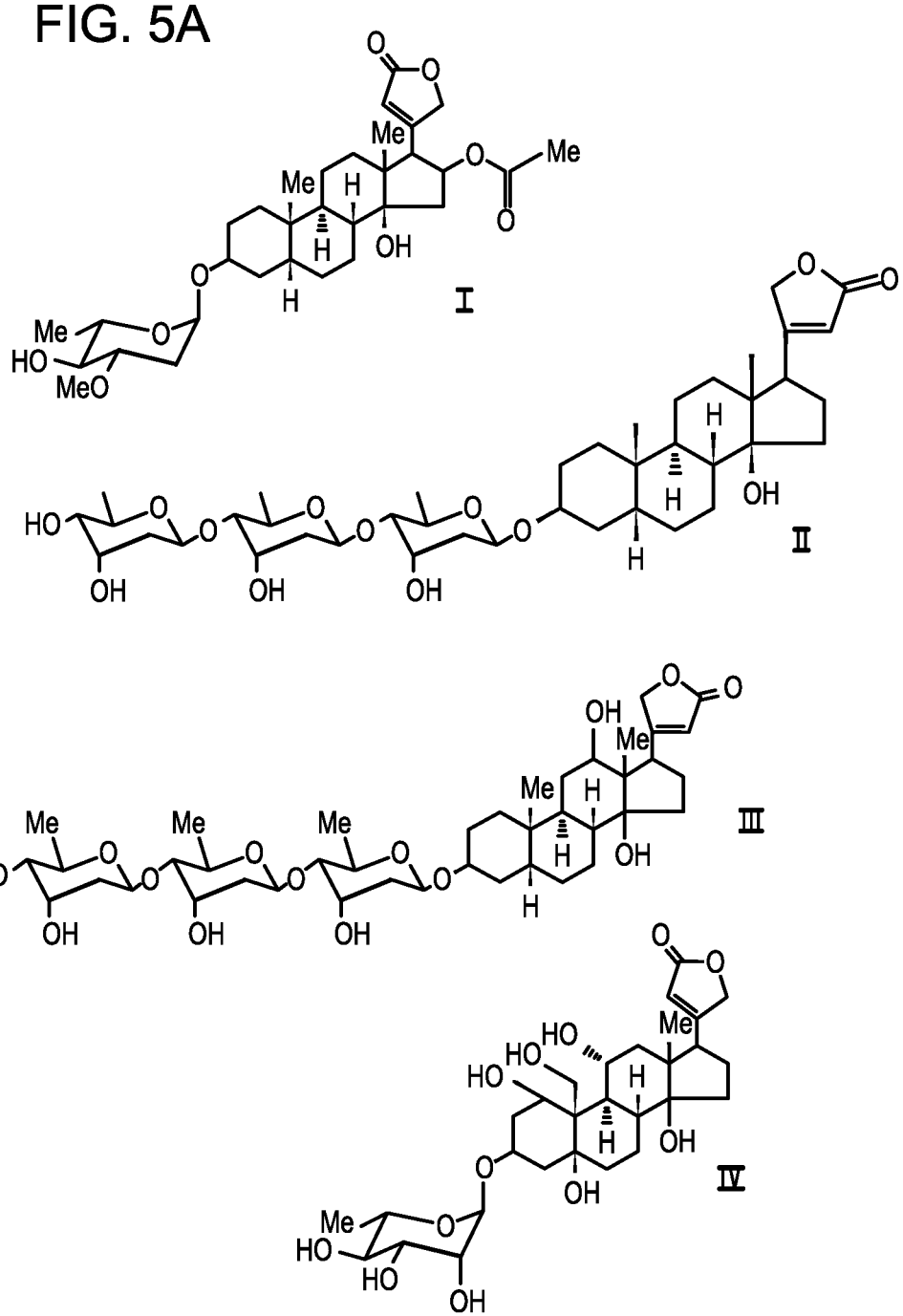

Seven compounds were identified as variants of oleandrin and tested for activity. The data are given in Table 1. The chemical structures of the compounds tested are shown in FIGS. 5A and 5B.

TABLE 1

Structure-Activity-Relation for Oleandrin-analogue inhibition of IL-8 secretion from cystic fibrosis epithelial cell line IB-3

| Compound # | Code # | Common Name | ID50, nM |
|---|---|---|---|
| I | (0.CFRx.2) | oleandrin | 1.0 |
| II | (3.D.5878) | digitoxin | 1.3 |
| III | (6.D.6003) | digoxin | 5.4 |
| IV | (7.O.3125) | ouabain | 8.0 |
| V | (4.D.9026) | digoxigenin | 17.0 |
| VI | (2.D.9404) | digitoxigenin | 25.0 |
| VII | (1.A.3259) | acetyl-stropanthidin | 60 |
| VIII | (5.D.7157) | digoxingenin, 3,12-diAc> | 1000 |

The assays are performed exactly as described above for oleandrin. As can be seen from the above data, the order of activity of each compound tested was found to be as follows: I, II>III, IV>V, VI>VII>>VIII.

From the above results, it appears that the mechanism of IL-8 suppression from CF cells by oleandrin is unique from other reported mechanisms of action as manifest by a different concentration sensitivity. The data show that spontaneous IL-8 secretion from CF lung epithelial cells occurs at the very low concentration of 1-2 nM. By contrast, the LD-50-defined toxicity of oleandrin is said to be equal to or greater than 0.6 uM. This high concentration is essentially the same range as that used by Manna, et al. (2000) to suppress TNFα-induced NFκB activation in human tumor cells. Aizman, et al. (2001) claim that ouabain (Compound IV; ID50=8 nM) activates NFkB at concentrations between 50 μM and 250 μM. This is 50,000-250,000 fold greater than the suppressive effects on IL-8 secretion from CF cells. Thus the therapeutic effect of oleandrin on IL-8 secretion from CF epithelial cells appears to be by a decidedly different mechanism than that manifest either on TNFα-evoked activation of NFκB, or cardiotoxicity in live animals. On the basis of the above data one can calculate the apparent therapeutic index, the ratio of concentrations associated with the therapeutic/toxic ratio. For oleandrin it is ca. 600 (i.e., the product of "600 nM/1 nM"). The therapeutic window for oleandrin, meaning the concentration range between therapeutic and toxic doses, is approximately 2.5 logs.

The therapeutic index of oleandrin and its solubility properties indicate that oleandrin has advantages over competitive candidate drugs currently under therapeutic consideration for cystic fibrosis. Competitive CF drugs which are known to affect IL-8 secretion from CF lung epithelial cells include the xanthines CPX (ID50=5 uM) and DAX (ID50=0.5 μM). Without questioning the potential value of these compounds, we can note that the concentrations needed for efficacy by these candidates is on the order of 1000-fold higher than that needed for oleandrin and certain of its analogues. In addition, the xanthines are challenging in terms of the concentrations needed to achieve therapeutic bioavailability. Finally, the xanthines must be administered in DMSO or a biocompatible hydrophobic vehicle, while oleandrin and its active analogues are soluble in ethanol.

The Structure-Activity Relationship (SAR) for oleandrin can be elucidated from consideration of the relative activities of structural analogues. As seen from the structures shown in FIGS. 5A and 5B, the most active species tested (i.e., Species I and Species II) are characterized by sugars of different structures and by the absence of oxygen-containing substitutions at or near the 12 position on the C ring. The next most active species (i.e., Species III and Species IV) are also characterized by sugars of different structures. However, Species III has an equatorial hydroxyl moiety on the 12 position of the C ring, while Species IV has an axial hydroxyl on the neighboring 11 position of the C ring. The next most active species (i.e., Species V and Species VI) have no sugars whatsoever. Species V also has an equatorial hydroxyl moiety on the 12 position of the C ring while Species VI lacks substitutions on this ring. The next most active species (i.e., Species VII) also lacks both sugars on the 3 position and substitutions on the C ring. However, it has an equatorial carbonyl on the 19 position between the A and B rings. In all other compounds except Species IV, this position is occupied by an equatorial methyl group. Finally, we come to Species VIII which appears to be entirely inactive even at a concentration of 1000 nM (1 micromolar). Species VIII is characterized by an equatorial acetyl group at the 12 position of the C ring, as well as an acetyl group on the 3 position. This position is usually occupied in other species by sugar moieties.

From the above data, it appears that the activity of oleandrin and its analogues is optimally promoted by (i) the presence of glycosyl moieties at the 3 position of the cholesterol nucleus and (ii) by the absence of oxygen-containing substitutions at or near the 12 position on the C ring. Activity appears to decline when (i) glycosyl moieties are absent from the 3 position and when (ii) oxygen-containing substitutions are made at or near the 12 position on the C ring. Additionally, activity is apparently altogether lost (e.g., Species VIII) when a bulky equatorial acetyl group is substituted at the 12 position. The equatorial 12 position and its neighbors therefore have negative pharmacophoric importance, whereas glycosidic substitution at the 3 position has a positive pharmacophoric importance for the control of IL-8 secretion from CF lung epithelial cells.

Potency, however, is not the only issue to consider when considering the advantage of one variant of a drug over another. Other considerations include half-life, bioavailability, dosage, compounding, host genetics, and possible side effects. Many of these cardiac glycosides have been used in humans for centuries and the potential side effects are therefore relatively well established. The relative efficacy of various species of cardiac glycosides for CF therapeutics can be determined by testing at the clinical level.

The present invention therefore provides a method of suppressing IL-8 secretion from CF lung epithelial cells using cardiac glycosides such as oleandrin. The present invention also provides a method of suppressing spontaneously high levels of IL-8 secretion from cells using cardiac glycosides such as oleandrin.

A method of treating disease conditions characterized by high levels of IL-8 secretion is also provided. Disease conditions characterized by high levels of IL-8 include the following: cardiopulmonary bypass risk following surgery, cardiopulmonary arrest, inflammatory bowel disease, atherosclerosis, noneosinophilic asthma, asthma, non-specific airway hyperresponsiveness, chronic pulmonary obstructive disease, nosocomial pneumonia, traumatic brain injury, stroke, cerebral reperfusion injury, endotoxemia-induced acute respiratory distress syndrome, diabetes, proliferative diabetic retinopathy, transplant graft rejection (including kidney transplant graft rejection, lung transplant graft rejection, pancreas transplant graft rejection, intestine transplant graft rejection, heart transplant graft rejection, bladder transplant graft rejection, multiple organ transplant graft rejection), Alzheimers Disease, Parkinson's Disease, HIV-1 infection, AIDS, HIV-1-associated dementia, viral infections, infection with adenovirus, infection with human rhino virus, infection with influenza virus, infection with herpes virus, cancer, cyclooxygenase-resistant fever, psoriasis, rheumatoid arthritis, Sjogren's syndrome, Behcet's disease, psoriatic arthritis, glomerulonephritis, thermal injury (e.g., thermal injury by sunburn), acute pancreatitis, smoke inhalation, acid injury to the lung, reexpansion pulmonary edema (REPE).

Also according to the invention, a method of administering a cardiac glycoside is provided in which the compound is immobilized in a biocompatible, biodegradable substance. The cardiac glycoside according to the invention can be immobilized in a biocompatible, biodegradable substance and administered locally by brachytherapy. The cardiac glycoside according to the invention can also be formulated as an intravenous solution. Alternatively, the cardiac glycoside can be formulated for oral administration (e.g., as an elixer, powder, tablet or capsule). The cardiac glycoside, for example, can be formulated for oral administration in an acid stable capsule.

The cardiac glycoside according to the invention is used for preparing a medicament for the treatment of disease conditions characterized by elevated levels of IL-8, wherein the cardiac glycoside is one of oleandrin and digitoxin and is for administration at dosages of about 1.0 nM for oleandrin or about 1.3 nM for digitoxin, adjusted to the mass of the recipient and the need of the recipient to reduce or inhibit the level of IL-8. The medicament can be formulated for administration by injection or for aerosol administration to the respiratory tract. Alternatively, the cardiac glycoside can be formulated as nose drops or as a nasal spray.

The cardiac glycoside according to the invention can also be formulated as a suppository or for dermal administration. For example, the cardiac glycoside can be formulated in a salve or as a solution for topical application or as a patch for transdermal or superdermal controlled or spontaneous release. The cardiac glycoside can also be formulated as a ear drops, eye drops, or as a gargle.

The cardiac glycoside can also be formulated as an implant in the central nervous system.

Compositions comprising cardiac glycosides and a pharmaceutically acceptable carrier and methods of treating using such compositions are also provided according to the invention.

From the foregoing, it will be appreciated that, although specific embodiments of the invention have been described herein for purposes of illustration, various modifications may be made without deviating from the spirit and scope of the invention.

REFERENCES

Abman, et al., "Early Bacteriologic, Immunologic, and Clinical Courses of Young Infants with Cystic Fibrosis Identified by Neonatal Screening", J. Pediatrics, 119, 211-217 (1991).

Aizman, O., et al., "Ouabain, a Steroid Hormone that Signals with Slow Calcium Oscillations", Proc. Nat. Acad. Sci. (USA), 98, 13420-13424 (2001).

Amin, et al., "Inflammation and Structural Changes in the Airways of Patients with Primary Sjogren's Syndrome, Respir. Med., 95, 11, 904-10 (2001).

Anderson, et al., "Generation of cAMP Activated Chloride Currents by Expression of CFTR", Science, 2516, 879-682 (1991).

Arispe, et al., "Alzheimer's Disease Amyloid B Protein Forms Calcium Channels in Bilayer Membranes: Blockade by Tromethamine and Aluminum, Proc. Nat. Acad. Sci. (USA), 90, 567-571 (1993).

Arispe, et al., "$Zn^{2+}$ Interaction with Alzheimer's Amyloid β-Protein Calcium Channels", Proc. Nat. Acad. Sci. (USA), 93, 1710-1715 (1996).

Arispe, et al., "Intrinsic Anion Channel Activity of the Recombinant First Nucleotide Binding Fold Domain of to Cystic Fibrosis Transmembrane Conductance Regulator Protein", Proc. Nat. Acad. Sci. (USA), 89, 1539-1543 (1992).

Arispe, et al., "Direct Activation of Cystic Fibrosis Transmembrane Conductance Regulator by 8-Cyclopentyl-1,3-Dipropylxanthine and 1,3-Diallyl-8-Cyclohexylxanthine", J. Biol. Chem., 273, 5724-5734 (1998).

Armstrong, et al., "Lower Airway Inflammation in Infants and Young Children with Cystic Fibrosis", Am. J. Respir. Crit. Care Med., 156, 1197-1204 (1997).

Bailey, et al., "Pharmacogenomics-It's Not Just Pharmacogenetics", Curr. Opin. Biotechnol., 6, 595-601 (1998).

Baldwin, et al., "The NF-κB and IκB proteins: New Discoveries and Insights", *Annu. Rev Immunol.* 14, 649-681 (1996).

Bear, et al., "cAMP-Activated Chloride Conductance in the Colonic Cell Line Caco-2", AM. J. Physiol., 262, C251-C256 (1992).

Bedard, et al., "Release of Interleukin-8, Interleukin-6, and Colony-Stimulating Factors by Upper Airways Epithelial Cells: Implications for Cystic Fibrosis", Am. J. Resp. Cell Mol. Biol., 9, 455-462 (1993).

Betz, R., et al., "Increased Sputum IL-8 and in Asymptomatic Airway Hyperresponsiveness", Lung, 179, 119-133 (2001).

Berger, et al., "Identification and Regulation of the Cystic Fibrosis Transmembrane Conductance Regulator-Generated Chloride Channel", J. Clin. Inv., 88, 1422-1431 (1991).

Bhatia, et al., "Inflammatory Mediators as Therapeutic Targets in Acute Pancreatitis", Curr. Opin. Investig. Drugs, 2, 496-501 (2001).

Bonfield, et al., "Normal Bronchial Epithelial Cells Constitutively Produce the Anti-Inflammatory Cytokine Interleukin 10, which is Downregulated in Cystic Fibrosis", Am. J. Respir. Mol. Biol., 13, 257-261 (1995a).

Bonfield, et al., "Inflammatory Cytokines in Cystic Fibrosis Lungs, Am. J. Respir. Crit. Care Med., 152, 2111-2118 (1995b).

Brasier, et al., "A Promoter Recruitment Mmechanism for Tumor Necrosis Factor-α-Induced Interleukin-8 Transcription in Type II Pulmonary Eepithelial Cells: Dependence on Nuclear Abundance of Rel-A, NF-κB, and c-Rel Transcription Factors", J. Biol. Chem., 273, 3551-3556 (1998).

Bretscher, et al., "Regulation of Cortical Structure by the Ezrin-Radaxin-Moesin Protein Family", Curr. Opin. Cell Biol., 11, 109-116 (1999).

Briars, et al., "Faecal Interleukin-8 and Tumour Necrosis Factor-Alpha Concentrations in Cystic Fibrosis", Arch. Dis. Child, 73, 74-76 (1995).

Brockman, et al., "Coupling of a Signal Response Domain in I Kappa B Alpha to Multiple Pathways for NF-Kappa B Activation", Mol. Cell. Biol., 15, 2809-2818 (1995).

Casavola, et al., "CPX a Selective A1-Adenocine-Receptor Antagonist, Regulates Intracellular pH in Cystic Fibrosis Cells", Am. J. Physiol., 269, C226-233 (1995).

Casola, et al., "Requirement of a Novel Upstream Response Element in Respiratory Syncytial Virus-Induced IL-8 Gene Expression", J. Immunol., 164, 5944-5951 (2000).

Cheng, et al., "Defective Intracellular Transport and Processing of CFTR is the Molecular Basis of Most Cystic Fibrosis", Cell, 63, 827-834 (1990).

Cohen, et al., "CPX (1,3-Dipropyl-8-Cyclopentyl xanthine) and other Alkyl-Xanthines Differentially Bind to the Wild Type and ΔF508 Mutant First Nucleotide Binding Fold (NBF-1) Domains of the Cystic Fibrosis Transmembrane Conductance Regulator (CFTR)", Biochemistry, 36, 6455-6461 (1997).

Collins, "Cystic Fibrosis Molecular Biology and Therapeutic Implication, Science, 256, 774-779 (1992).

Courchesne, et al., "Comparison of In-Gel and On-Membrane Digestion Methods at Low to Sub-pmol Level for Identification of Gel-Separated Proteins", Electrophoresis, 18, 369-381 (1997).

Courchesne, et al., "Optimization of Capillary Chromatography Ion Trap Mass Spectrometry for Identification of Gel-Separated Proteins", Electrophoresis, 19, 956-967 (1998).

Cruse, et al., *Illustrated Dictionary of Immunology*, CRC Press, Boca Raton, Appendix 3 (1995).

Dean, et al., "Interleukin-8 Concentrations are Elevated in Bronchoalveolar Lavage, Sputum, Ans Sera of Children with Cystic Fibrosis", Pediatr. Res., 34, 159-161 (1993).

Dimango, et al., "Diverse *Pseudomonas Aeruginosa* Gene Products Stimulate Respiratory Epithelial Cells to Produce Interleukin-8.", J. Clin. Invest., 96, 2204-2210 (1995).

DiMango, et al., "Activation of NF-kappaB by Adherent *Pseudomonas Aeruginosa* in Normal and Cystic Fibrosis Respiratory Epithelial Cells", J. Clin. Invest., 101, 2598-2605 (1998).

DeFranco, et al., "Macrophage Signaling in Response to Bacterial Lipopolysaccharides", Pediatric Pulm., S19, 124 (1999).

Denning, et al., "Localization of Cystic Fibrosis Transmembrane Conductance Regulator in Chloride Secretory Epithelia", J. Clin. Inv., 89, 339-349 (1992b).

Dignam, et al., "Accurate Transcription Initiation by RNA Polymerase II in a Soluble Extract from Isolated Mammalian Nuclei", Nucleic Acid. Res., 11, 1475-1489 (1983).

Drabe, et al., "Genetic Predisposition in Patients Undergoing Cardiopulmonary Bypass Surgery is Associated with an Increase of Inflammatory Cytokines", Eur. J. Cardiothorac. Surg., 20, 609-613 (2001).

Drumm, et al., "Chloride Conductance Expressed by DF508 and other Mutant CFTRs in *Xenopus Oocytes*", Science, 254, 1797-1799 (1991).

Eidelman, et al., "A1-Adenosine-Receptor Antagonists Activate Chloride Efflux from Cystic Fibrosis Cells", Proc. Nat. Acad. Sci. (USA), 89, 5562-5566 (1992).

Eidelman, et al., "Role for Aberrant Phospholipid Interactions in the Trafficking Defect of ΔF508-Cystic Fibrosis Transmembrane Conductance Regulator (CFTR)", Biochemistry, in review (2002).

Eidelman, et al., "Genes from the TNFaR/NFkB Pathway Control the Pro-Inflammatory State in Cystic Fibrosis Epithelial Cells", Molecular Medicine, 7, 523-534 (2001a)

Eisen, et al., "Cluster Analysis and Display of Genome-Wide Expression Patterns", Proc. Nat. Acad. Sci. (USA), 95, 14863-14868 (1998).

Engelhardt, J. G., et al., "Submucosal Glands are the Predominant Site of CFTR Expression in the Human Bronchus", Nature Genetics, 2, 240-247 (1992).

Egan, et al., "Defective Regulation of Outwardly Rectifying Cl Channels by Protein Kinase A Corrected by Insertion of CFTR", Nature, 358, 581-584 (1992).

Elner, et al., "Cytokines in Proliferative Diabetic Retinopathy and Proliferative Vitreoretinopathy", Curr. Eye Res., 14, 1045-1053 (1995).

Ertenli, et al., "Synovial Fluid Cytokine Levels in Behcet's Disease, Clin. Exp. Rheumatol. Suppl., 24, S37-41 (2001).

Elner, et al., "Interferon-Induced Protein 10 and Interleukin 8. C-X-C Chemokines Present in Proliferative Diabetic Retinopathy", Arch. Ophthal., 116, 1597-1601 (1998).

Fisher, et al., "Elevated Levels of Interleukin-8 in Donor Lungs is Associated with Early Graft Failure After Lung Transplantation, Am. J. Respir. Crit. Care Med., 163, 259-265 (2001).

Fried, et al., "Equilibria and Kinetics of Lac Repressor-Operator Interactions by Polyacrylamide Gel Electrophoresis, Nucleic Acid Res., 9, 6505-6510 (1981).

Gales, et al., "A. DNAse Footprinting: A Simple Method for the Detection of Protein-DNA Binding Specificity", Nucleic Acid Res., 5, 3157-3170 (1978).

Gao, et al., "Inhibition of Interleukin-8 Synthesis by Intraarticular Methotrexate Therapy in Patients with Rheumatoid Arthritis", Z. Rheumatol., 57, 95-100 (1998).

Garofalo, et al., "Transcriptional Activation of the Interleukin-8 Gene by Respiratory Syncytial Virus Infection in Alveolar Epithelial Cells: Nuclear Translocation of the RelA Transcription Factor as a Mechanism Producing Airway Mucosal Inflammation", J. Virol., 70, 8773-8781. (1996).

Goping, et al., "MPTP Destroys a Specific Tyrosine Hydroxylase-Positive Dopaminergic Nucleus in the Goldfish Forebrain: Specific Protection by L-Deprenyl but not Clorgyline", Brain Research, 687, 35-52 (1995).

Grunblatt, et al., "Gene Expression Analysis in N-Methyl-4-Phenyl-1,2,3,6-Tetrahydropyridine Mice Model of Parkinson's Disease Using cDNA Microarray: Effect of R-Apomorphine", J. Neurochem, 78, 1, 1-12 (2001).

Guay-Broder, et al., "A-1 Receptor Antagonist "Cyclopentyl-1,3-Dipropylxanthine Selectively Activates Chloride Efflux from Human Epithelial and Mouse Fibroblast Cell Lines Expressing the Cystic Fibrosis Transmembrane Regulator ΔF508 Mutation", Biochemistry, 34, 9079-9087 (1995).

Gibson, et al., "Heterogeneity of Airway Inflammation in Persistent Asthma: Evidence of Neutrophilic Inflammation and Increased Sputum Interleukin-8, Chest, 119, 1329-1336 (2001).

Gitter, et al., "Amyloid beta Peptide Potentiates Cytokine Secretion by Interleukin-1 Beta Activated Human Astrocytoma Cells", Proc. Nat. Acad. Sci. (USA), 92, 10738-10741 (1995).

Gilmour, et al., "Adenoviral E1A Primes Alveolar Epithelial Cells to PM(10)-Induced Transcription of Interleukin-8, Am. J. Physiol. Lung Cell Mol. Physiol., 281, L598-606 (2001).

Ferrari, et al., "Pharmacogenomics: A New Approach to Individual Therapy of Hypertension?", Curr. Opin. Nephrol. Hypertens, 7, :217-221 (1998).

Francoeur, C., et al., "Nitric Oxide and Interleukin-8 as Inflammatory Components of Cystic Fibrosis", Inflammation, 19, 587-598 (1995).

Fulmer, et al., "Two Cystic Fibrosis Transmembrane Conductance Regulator Mutations Have Different Effects on Both Pulmonary Phenotype and Regulation of Outwardly Rectified Chloride Currents", Proc. Nat. Acad. Sci. (USA), 92, 6832-6836 (1995).

Gabriel, et al., "CFTR and Outward Rectifying Chloride Channel are Distinct Proteins with a Regulatory Relationship", Nature, 363, 263-268 (1993).

Gottlieb, et al., "Mutant Cystic Fibrosis Transmembrane Conductance Regulator Inhibits Acidification and Apoptosis in C127 Cell: Possible Relevance to Cystic Fibrosis", Proc. Nat. Acad. Sci. (USA), 93, 3587-3591 (1996).

Graever, et al., "Genomic Profiling of Drug Sensitivities Via Induced Haploinsufficiency", Nat. Genet., 3, 278-283 (1999).

Griesenbach, et al., "Towards Anti-Inflammatory Lung Gene Therapy", Pediatric Pulm., S19, 237 (1999a).

Griesenbach, et al., "Anti-Infammatory Gene Therapy Directed at the Airway Epithelium", Gene Therapy, 7:306-313 (2000).

Hayashida, et al., "Synovial Stromal Cells from Rheumatoid Arthritis Patients Attract Monocytes by Producing MCP-1 and IL-8", Arthritis Res., 3, 118-126 (2001).

Kraan, et al., "The Development of Clinical Signs of Rheumatoid Synovial Inflammation is Associated with Increased Synthesis of the Chemokine CXCL8 (interleukin-8)", Arthritis Res, 3:65-71 (2001).

Hoxtermann, et al., "Fumaric Acid Esters Suppress Peripheral CD4- and CD8-Positive Lymphocytes in Poriasis", Dermatology, 196, 223-230 (1998).

Imada, et al., "Coordinate Upregulation of Interleukin-8 and Growth-Related Gene Product-Alpha is Present in the Colonic Mucosa of Inflammatory Bowel", Scand. J. Gastroent., 36, 854-864 (2001).

Inoue, et al., "Adenoviral-Mediated Gene Therapy of Human Bladder Cancer with Antisense Interleukin-8", Oncol. Rep., 8, 955-964 (2001).

Ionoco, et al., "Interleukin-8 Levels and Activity in Delayed-Healing Human Thermal Wounds, Wound Repair Regeneration, 8, 216-225 (2000).

Ismailov, et al., "Regulation of Epithelial Sodium Channel by the Cystic Fibrosis Transmembrane Conductance Regulator", J. Biol. Chem., 271, 4725-4732 (1996).

Ito, et al., "Significance of Elevated Serum Interleukin-8 in Patients Resuscitated After Cardiopulmonary Arrest, Resuscitation, 51, :47-53 (2001).

Kartner, et al., "Mislocalization of ΔF508 CFTR in Cystic Fibrosis Sweat Gland", Nature Genetics, 1, 321-327 (1992).

Kent, et al., "Eukaryotic Phospholipid Biosynthesis", Ann. Rev. Biochem., 64, 315-343 (1995).

Koch, et al., "Regulation of Angiogenesis by the C-X-C Chemokines Interleukin-8 and Epithelial Neutrophil Activating Peptide 78 in the Rheumatoid Joint", Arthritis Rheum., 44, :31-40 (2001).

Konig, et al., "Inflammatory Infiltrate and Interleukin-8 Expression in the Synovium of Psoriatic Arthritis—An Immunohistochemical and mRNA Analysis", Rheumatol. Int., 17, 159-68 (1997).

Jacobson, et al., "Stimulation by Alkylxanthines of Chloride Efflux in CFPAC-1 Calls Does not Involve A, Adenosine Receptors", Biochemistry, 34, 9088-9094 (1995).

Jovov, et al., "Cystic fibrosis Transmembrane Conductance Regulator is required for Protein Kinase A Activation of an Outwardly Rectified Anion Channel Purified from Bovine Tracheal Epithelia", J, Biol. Chem., 270, 1521-1528 (1995).

Kossman, et al., "Interleukin-8 Released Into Cerebrospinal Fluid After Brain Injury is Associated with Blood-Brain Barrier Dysfunction and Nerve Growth Factor Production, J. Cerebr. Blood Flow Metab., 17, 280-289 (1997).

Kostulas, et al., "Increased IL-1beta, IL-8 and IL-17 mRNA Expression in Blood Mononuclear Cells Observed in a Prospectiveiischemic Stroke Study, Stroke, 30, 2174-2179 (1999).

Kruger, et al., "Genetic Analysis of Immunomodulating Factors in Sporadic Parkinson's Disease", J. Neural. Trans., 2000; 107, 553-562 (2000).

Kutsch, et al., "Induction of the Chemokines Interleukin-8 and IP-10 by Human Immunodeficiency Virus Type 1 tat in astrocytes", J. Virol., 74, 9214-9221 (2000).

Kadonaga, et al., "Affinity Purification of Sequence-Specific DNA Binding Proteins", Proc. Nat. Acad. Sci. (USA), 83, 889-893 (1986).

Kartner, et al., "Expression of the Cystic Fibrosis Gene in Non-Epithelial Invertebrate Cells Produce a Regulated Anion Conductance", Cell, 64, 681-691 (1991).

Kartner, et al., "Mislocalization of ΔF508 CFTR in Cystic Fibrosis Sweat Gland", Nature Genetics, 1, 321-327 (1992).

Kerem, et al., "Identification of the Cystic Fibrosis Gene: Genetic Analysis", Science, 245, 1073-1080 (1998).

Kingsbury, et al., *Poisonous Plants of the United States and Canada*, Prentice-Hall, Inc. Englewood Cliff, N.J., 626 (1964).

Klingenhoff, et al., "Functional Promoter Modules Can Be Detected by Formal Models Independent of Overall Nucleotide Similarity", Bioinformatics, 15, 180-186 (1999).

Konstan, et al., "Effect of High Dose Ibuprofen in Patients with Cystic Fibrosis", New Eng. J. Med., 332, 848-854 [and comments in same journal: 332: 886-887; 333: 731-732 (1995).

Laffon, et al., "Interleukin-8 Mediates Injury from Smoke Inhalation to Both the Lung Epithelial and Alveolar Epithelial Barriers in Rabbits", Am. J. Respir. Crit. Care Med., 160, 1443-1449 (1999).

Lamprecht, et al., "The Role of NHERF and E3KARP in the cAMP-Mediated Inhibition of NHE3, J. Biol. Chem., 273, 29972-29978 (1998).

Link, et al., "Direct Analysis of Protein Complexes Using Mass Spectroscopy, Nature Biotechnology, 17, 676-682 (1999).

Lipsky, et al., "Rheumatoid Arthritis", Harrisons Principles of Internal Medicine, 15th edition (eds, Braunwald, et al.) McGraw-Hill, Pubs., New York, 1929-1937 (2001).

Lukacs, et al., "Conformational Maturation of CFTR but not Its Mutant Counterpart (ΔF508) Occurs in the Endoplasmic Reticulum and Requires ATP", EMBO J., 13, 6076-6086 (1994).

Maier, et al., "Differential Release of Interleukines 6, 8, and 10 in Cerebrospinal Fluid and Plasma After Traumatic Brain Injury", Shock, 15, 421-426 (2001).

Mandel, et al., "cDNA Microarray to Study Gene Expression of Dopaminergic Neurodegeneration and Neuroprotection in MPTP and 6-Hydroxydopamine Models: Implications for Idiopathic Parkinson's Disease", J. Neural. Transm. Suppl., 117-124 (2000).

Manna, et al., "Oleandrin Suppresses Activation of Nuclear Transcription Factor-kB, Activator Protein-1 and c-Jun NH2-Terminal Kinase, Cancer Research, 60, 3838-3847 (2000).

Marguet, et al., "Eosiniophilcation Protein and Interleukin-8 Levels in Bronchial Lavage Fluid from Children with Asthma and Infantile Wheeze", Pediatr. Allergy Immunol., 12, 27-33 (2001).

Matsumoto, et al., "Pivotal Role of Interleukin-8 in the Acute Respiratory Distress Syndrome and Cerebral Reperfusion Injury", J. Leukoc. Biol., 62, 581-587 (1997a).

Matsumoto, et al., "Prevention of Cerebral Edema and Infarct in Cerebral Reperfusion Injury by an Antibody toIinterleukin-8", Lab Invest., 77, 119-125 (1997b).

Modelska, et al., "Acid-Induced Lung Injury. Protective Effect of Anti-Interleukin-8 Pretreatment on Alveolar Epithelial Barrier Function in Rabbits", Am. J. Respir. Crit. Care Med., 160, 1441-1442 (1999).

Morel, et al., "Interleukin-18 Induces Rheumatoid Arthritis Synovial Fibroblast CXC Chemokine Production Through NFkappaB Activation", Lab Invest., 81, 1371-1383 (2001).

Moyer, et al., "A PDZ Interacting Domain in CFTR is Required for Apical Polarization and Export from the Endoplasmic Reticulum", Pediatric Pulm, S19, 164 (1999a).

Moyer, et al., "PDZ Interacting Domain in CFTR is an Apical Membrane Polarization Signal", J. Clin. Inv., 104, 1353-1361 (1999b).

Muehlstedt, et al., "Cytokines and Pathogenesis of Nosocomial Pneumonia", Surgery, 130, 602-609 (2001).

Mukaida, et al., "Inhibition of Neutrophil-Mediated Acute Inflammation Injury by an Antibody Against Interleukin-8 (IL-8), Inflamm. Res. Suppl., 3, S151-157 (1998).

Murayama, et al., "The Immediate Early Gene 1 Product of Human Cytomegalovirus is Sufficient for Upregulation of Interleukin-8 Gene Expression", Biochem. Biophys. Res. Comm., 279, 298-304 (2000).

Nandate, et al., "Cerebrovascular Cytokine Response During Coronary Artery Bypass Surgery: Specific Production of Interleukin-8 and its Attenuation by Hypothermic Cardiopulmonary Bypass", Anesth. Analg., 89, 823-828 (1999).

Nakamura, et al., Am. J. Respir. Crit. Care Med., 161, 1030-1036 (2000).

Nanki, et al., "Chemokines Regulate IL-6 and IL-8 Production by Fibroblast-Like Synoviocytes from Patients with Rheumatoid Arthritis", J. Immunol., 167, 5381-5385 (2001).

Naren, A. P., Nelson, D. J., Xie, W., Jovov, B., Pevsner, J., Bennett, M. K., Benos, D. J., Quick, M. W., and Kirk, K. L. (1997) Regulation of CFTR chloride channels by syntaxin and Munc18 isoforms. Nature 390:302-305.

Naren, A. P., Quick, M. W., Collawn, J. G., Nelson, D. J., and Kirk, K. L. (1998) Syntaxin IA inhibits CFTR chloride channels by means of domain-specific protein-protein interactions. Proc. Nat. Acad. Sci. (USA) 95:10972-10977.

Nishimura, et al., "Tumor Necrosis Factor Gene Polymorphisms in Patients with Sporadic Parkinson's Disease", Neurosci. Lett., 311, 1-4 (2001).

Nourbakhsh, et al., "The NF-KappaB Repressing Factor NRF is Involved in Basal Repression and Interleukin (IL)-1-Induced Activation of IL-8 Transcription by Binding to a Conserved NF-KappaB-Flanking Sequence Element", J. Biol. Chem., 44, 4501-4508 (2000).

Olszewski, et al., "Lymph Draining from Foot Joints in Rheumatoid Arrthritis Provides Insight into Local Cytokine and Chemokine Production and Transport to Lymph Nodes", Arthritis Rheum., 44, 54.1-549 (2001).

Osman, et al., "A Monoclonal Anti-Interleukin-8 Antibody (WS-4) Inhibits Cytokine Response and Acute Lung Injury in Experimental Severe Acute Necrotising Pancreatitis in Rabbits", Gut, 43, 232-239 (1988).

Osman, et al., "Graded Experimental Acute Pancreatitis: Monitoring of a Renewed Rabbit Model Focusing on the Production of Interleukin-8 (IL-8) and CD11b/CD18", Eur. J. Gastroenterol. Hepatol., 11, 137-149 (1999).

Ott, et al., "Cytokines and Metabolic Dysfunction after Severe Head Injury", J. Neurotrauma, 11, 447472 (1994).

Pearson, et al., "Structure of the ERM Protein Moesin Reveals the FERM Domain Fold Masked by an Extended Actin Binding Tail Domain", Cell, 101, 259-270 (2000).

Pier, et al., "Role of Mutant CFTR in Hypersusceptibility of Cystic Fibrosis Patients to Lung Infections", Science, 271, 64-67 (1996).

Pilewski, et al., "Role of CFTR in Airway Disease", Physiol. Rev., 79, S215-S255 (1999).

Pollard, et al., "Anatomical Genomics: Systems of Genes Underlying the Biology of Systems", Anatomical Rec., 259, :iii-ix (2000).

Pollard, et al., "A Parkinsonian Syndrome Induced in the Goldfish by the Neurotoxin MPTP", FASEB J., 6, 3108-3116 (1992).

Pollard, et al., "Role of CPX in Promoting Trafficking and Chloride Channel Activity of Wildtype and Mutant CFTR", Pediatric Pulmonology, S14, 128-131 (1997).

Preston, M. J., et al., "Rapid and Sensitive Method for Evaluating Pseudomonas Aeruginosa Virulence Factors During Corneal Infections in Mice", Infect. Immun., 63, 3497-3501 (1995).

Richman-Eisenstat, et al., "Interleukin-8: an Important Chemoattractant in Sputum of Patients with Chronic Inflammatory Airway Diseases", Am. J. Physiol., 264, L413-418 9 (1993).

Raghuram, V., et al., "Multiple PDZ Domains Involved in the Association of NHERF with CFTR", Pediatric Pulm., S19, 178 (1992).

Riordan, et al., "Identification of the Cystic Fibrosis Gene: Cloning and Characterization of Complementary DNA", Science, 245, 1066-1073 (1989).

Rodenburg, et al. "Superinduction of Interleukin 8 mRNA in Activated Monocyte Derived Macrophages from Rheumatoid Arthritis Patients", Ann. Rheum. Dis., 58. 648-52 (1999).

Rodriguez, et al., "Correlation of the Local and Systemic Cytokine Response with Clinical Outcome Following Thermal Injury", J. Trauma, 34, 684-694 (1993).

Roebuck, et al, K. A., "Regulation of Interleukin-8 Gene Expression, J. Interferon Cytokine Res., 19, 429-438 (1999).

Rommens, et al., "Identification of the Cystic Fibrosis Gene: Chromosome Walking and Jumping", Science, 245, 1, 1059-1065 (1989).

Rothe, et al., "Human Osteoclasts and Osteoclast-Like Cells Synthesize and Release High Basal and Inflammatory Stimulated Levels of the Potent Chemokine Interleukin-8", Endocrinology, 139, 4353-4363 (1998).

Ruef, et al., "Regulation of Cytokine Secretion by Cystic Fibrosis Airway Epithelial Cells", Eur. Resp. J., 6, 1429-1436 (1993).

Schultz, et al., "Pharmacology of CFTR Chloride Channel Activity", Physiol. Rev., 79, S109-S144 (1999).

Schultz, et al., "IBMX Stabilizes the ATP-Bound State of ΔF508-CFTR", J. Gen. Physiol., 104, 35a (1994).

Schwiebert, et al., "Chemokine expression in CF Epithelia: Implications for the Role of CFTR in RANTES Expression", Am. J. Physiol., 276, C700-710 (1999).

Shak, et al., "Recombinant Human DNAseI I Reduces Viscosity of Cystic Fibrosis Sputum", Proc. Nat. Acad. Sci. (USA), 87, 9188-9192 (1990).

Sherwood, et al., Interleukin-8, Neuroinflammation, and Secondary Brain Injury", Crit. Care Med., 28, 1221-1223 (2000).

Shirayoshi, et al., "Binding of Multiple Nuclear Factors to the 5' Upstream Regulatory Element of the Murine Major Histocompatibility Class I Gene", Mol. Cell. Biol., 7, 4542-4548 (1987).

Short, et al., "An Apical PDZ Protein Anchors the Cystic Fibrosis Transmembrane Conductance Regulator to the Cytoskeleton", J. Biol. Chem. 273, 19797-19801 (1998).

Stangl, et al., "Influence of Brain Death on Cytokine Release in Organ Donors and Renal Transplants". Transplant. Proc., 33, 1284-1285 (2001).

Stein, et al., "Distinct Mechanisms for Regulation of the Interleukin-8 Gene Involve Synergism and Cooperativity Between C/EBP and NF-Kappa B., Mol. Cell. Biol., 13, 7191-7198 (1993).

Stoof, et al., "The Antipsoriatic Drug Dimethylfumarate Strongly Suppresses Chemokine Production in Human Karatinocytes and Peripheral Blood Mononuclear Cells", Br. J. Dermatol. 144:1114-1120 (2001).

Stutts, et al., "CFTR as a cAMP-Dependent Regulator of Sodium Channels", Science, 269, 847-850 (1995).

Subauste, et al., "Effects of Tumor Ecrosis Factor Alpha, Epidermal Growth Factor and Transforming Growth Factor Alpha on Interleukin-8 Production by, and Human Rhinovirus Replication in, Bronchial Epithelial Cells", Int. Immunopharmacol., 1, 1229-1234 (2001).

Srivastava, et al., "Pharmacogenomics of the Cystic Fibrosis Transmembrane Conductance Regulator (CFTR) and the Cystic Fibrosis Drug CPX Using Genome Microarray Analysis", Molecular Med., 5, 753-767 (1999).

Srivastava, et al., "Low in vivo Levels of Human Anx7 (Annexin VII) Gene Expression are Due to Endogenous Inhibitory Promoter Sequences", Cell Biology Internat., 24, 475-481 (2000).

Suzuki, et al., "Tax protein of HTLV-1 Interacts with the Rel Homology Domain of NFkB p65 and c-Rel Proteins Bound to the NFkB Binding Site and Activates Transcription, Oncogene, 9, 3099-3105 (1994).

Sun, et al., "The PDZ Domain-Containing Protein E3KARP Couples EZRIN to Cystic Fibrosis Transmembrane Conductance Regulator (CFTR)", Pediatric Pulm., S19, 164 (1994).

Tabary, et al.," Selective Upregulation of the Chemokine IL8 Expression in Cystic Fibrosis Bronchial Gland Cells in vivo and in vitro", Am. J. Path., 153, 921-930 (1998).

Takahashi, et al., "The Participation of IL-8 in the Synovial Lesions at an Early Stage of Rheumatoid Arthritis", Tohoku J Exp Med., 188, 75-87 (1998).

Takata, et al., "Prevastatin Suppresses Interleukin-8 Production Induced by Thrombin in Human Aortic Endothelial Cells Cultures with High Glucose by Inhibiting the p44/42 Mitogen Activated Protein Kinase", Br. J. Pharm., 134, 753-762 (2001).

Tanaka, et al., "Medium-Chain Fatty Acids Stimulate Interleukin-8-Production in Caco-2 Cells with Different Mechanisms from Long Chain Fatty Acids, J. Gastroent. Hepatol., 16, 748-754 (2001).

Tarkowski, et al., "Intrathecal Release of Pro- and Anti-Inflammatory Cytokines During Stroke", Clin. Exp. Immunol., 110, 492-499 (1997).

Temaru, et al., "High Glucose Enhances the Gene Expression of Interleukin-8 in Human Endothelial Cells, but not Smooth Muscle Cells: Possible Role of Interleukin-8 in Diabetic Macroangiopathy", Diabetologia, 40, 610-613 (1997).

Troughton, et al., "Synovial Fluid Interleukin-8 and Neutrophil Function in Rheumatoid Arthritis and Seronegative Polyarthritis", Br. J. Rheumatol., 35, 1244-1251 (1996).

Tsui, et al., "Mutations and Sequence Variations Detected in the Cystic Fibrosis Transmembrane Conductance Regulator (CFTR) Gene: A Report from the Cystic Fibrosis Genetic Analysis Consortium", Hum. Mut., 1, 197-203 (1992a).

Tsui, et al., "The Spectrum of Cystic Fibrosis Mutations", Trends in Genetics, 8, 392-398 (1992b).

Vandermeeren, et al., "Dimethylfumarate is an Inhibitor of Cytokine-Induced Nuclear Translocation of NFkB1, but Not RelA in Normal Human Dermal Fibroblast Cells", J. Invest. Dermatol., 116, 124-130 (2001).

Victor, et al., "CCAAT Box Enhancer Protein Alpha (C/EBP-alpha) Stimulates KappaB Element-Mediated Transcription in Transfected Cells", J. Biol. Chem., 271, 5595-5602 (1996).

Vindenes, et al., "Increased Levels of Circulating Interleukin-8 in Patients with Large Burns: Relation to Burn Size and Sepsis", J. Trauma, 39, 635-640 (1995).

Wang, N., et al., Interleukin-8 is Induced by Cholesterol Loading of Macrophages and Expressed by Macrophage Foam Cells in Human Atheroma", J. Biol. Chem., 271, 8837-8842 (1996).

Ward, et al., "Intracellular Turnover of Cystic Fibrosis Transmembrane Conductance Regulator. Inefficient Processing and Rapid Degradation of Wildtype and Mutant Protein, J. Biol. Chem., 269, 25710-25718 (1994).

Ward, et al., "Degradation of CFTR by the Ubiquitin-Proteosome Pathway. Cell, 83, 121-127 (1995).

Welsh, et al., "Cystic Fibrosis", The Metabolic and Molecular Bases of Inherited Diseases, Scriver, et al., eds.), $7^{th}$ edition, 3799-3876, McGraw-Hill, New York (1995).

Whalen, et al., "Interleukin-8 is Increased in Cerebrospinal Fluid of Children with Severe Head Injury", Crit. Care Med., 28, 1221-1234 (2000).

Wu, et al., "CCAAT/Enhancer-Binding Protein (C/EBP) Bind to Overlapping Elements Within the Interleukin-8 Promoter. The role of Oct. 1 as a Transcriptional Repressor", J. Biol. Chem., 272, 2396-2403 (1997).

Xia, et al., "Interleukin-8 Receptor Immunoreactivity in Brain and Neuritic Plaques of Alzheimer's Disease", Am. J. Path., 150, 1267-1274 (1997).

Yang, et al., "The Common Variant of Cystic Fibrosis Transmembrane Conductance Regulator is Recognised by Hsp70 and Degraded in a Pre-Golgi Non-Lysosomal Compartment", Proc. Nat. Acad. Sci. (USA), 90, 9480-9484 (1993).

Yeh, et al., "Changes in Levels of IL-8 in Burned Patients", Burns, 23, 555-559 (1997).

Yoshida, et al., "Inhibition of IL-6 and IL-8 Induction From Cultured Rheumatoid Synovial Fibroblasts by Treatment with Aurothioglucose", Int. Immunol., 11, 151-158 (1997).

Yuuki, et al., "Inflammatory Cytokines in Vitreous Fluid and Serum of Patients with Diabetic Retinopathy", J. Diabetes Complications, 15, 257-259 (2001).

Zampronio, et al., "IInterleukin-8 Induces Fever by a Prostaglandin-Indepoendent Mechanism", Am. J. Physiol., 266, R1670-1674 (1994).

Zeitlin, et al., "A Cystic Fibrosis Bronchial Epithelial Cell Line: Immortalization by Adenol2-SV40 Infection", Am. J. Respir. Cell Mol. Biol., 4, 313-319 (1991).

Zhang, et al., "CPX Affects Expression and Trafficking of AF508-CFTR. Pediatric Pulm., S19, 182 (1999).

Zivna, et al., The Role of Cytokines and Antioxidant Status in Graft Quality Prediction", Transpl. Proc., 31, 2094 (1999).

Zozulinska, et al., Serum Interleukin-8 Level is Increased in Diabetic Patients", Diabetologia, 42, 117-118 (1998).

What is claimed is:

1. A method of treating a patient in need of treatment for a disease condition caused or aggravated by an excessive level of IL-8, comprising administering a cardiac glycoside that lacks an oxygen-containing substituent at both C11 and C12 and has glycosyl moieties at the C3 position, wherein the cardiac glycoside is administered at a concentration of from about 1 nM to about 2 nM, adjusted to the mass of the recipient and the need of the recipient to inhibit or reduce the level of IL-8.

2. The method according to claim 1, wherein the cardiac glycoside is selected from the group consisting of oleandrin and digitoxin.

3. The method according to claim 1, wherein the cardiac glycoside is digitoxin.

4. The method according to claim 1, wherein the cardiac glycoside is oleandrin.

5. The method according to claim 2, wherein the disease condition is cystic fibrosis, cardiopulmonary bypass surgery, cardiopulmonary arrest, inflammatory bowel disease, lung disorders and lung conditions, traumatic brain injury, stroke, cerebral reperfusion injury, transplant graft rejection, Alzheimer's disease, viral infections, fevers, psoriasis, arthritis, Sjogren's syndrome, Behcet's disease, Parkinson's disease, or glomerulonephritis.

6. The method according to claim 5, wherein the lung disorders and lung conditions comprise asthma, noneosinophilic asthma, non-specific airway hyper-responsiveness, chronic pulmonary obstructive disease, nosocomial pneumonia, endotoxemia-induced acute respiratory distress syndrome or related conditions.

7. A method of treating a mammal in need of treatment for disease conditions characterized by elevated levels of IL-8, comprising administering an effective amount of a cardiac glycoside having glycosyl moieties at the C3 position and lacking an oxygen-containing substituent at both C11 and C12 wherein the effective amount is a concentration of from about 1 nM to about 2 nM, adjusted to the mass of the recipient and the need of the recipient to reduce or inhibit the level of IL-8.

8. The method according to claim 7, wherein the cardiac glycoside is oleandrin.

9. The method according to claim 7, wherein the cardiac glycoside is digitoxin.

10. The method according to claim 7, wherein the disease condition is: cystic fibrosis, cardiopulmonary bypass surgery; cardiopulmonary arrest; inflammatory bowel disease; lung disorders and lung conditions; traumatic brain injury; stroke; cerebral reperfusion injury; transplant graft rejection; Alzheimer's disease; viral infections; fevers; psoriasis; arthritis; Sjogren's syndrome; Behcet's disease; Parkinson's disease; or glomerulonephritis.

11. The method according to claim 7, wherein the lung disorders and lung conditions comprise asthma, noneosinophilic asthma, non-specific airway hyper-responsiveness, chronic pulmonary obstructive disease, nosocomial pneumonia, endotoxemia-induced acute respiratory distress syndrome or related conditions.

12. A method for inhibiting or reducing the secretion of IL-8 from a cell secreting elevated levels of IL-8, comprising administering a cardiac glycoside in a concentration of from about 1 nM to about 2 nM, adjusted to the mass of the recipient and the need of the recipient to reduce or inhibit the level of IL-8, and wherein the cardiac glycoside has glycosyl moieties at the C3 position and lacks an oxygen-containing substituent at both C11 and C12.

13. The method according to claim 12, wherein the cardiac glycoside is oleandrin.

14. The method according to claim 12, wherein the cardiac glycoside is digitoxin.

15. The method according to claim 12, wherein the cardiac glycoside is for use in the treatment of a condition that is: cystic fibrosis, cardiopulmonary bypass surgery; cardiopulmonary arrest; inflammatory bowel disease; lung disorders and lung conditions; traumatic brain injury; stroke; cerebral reperfusion injury; transplant graft rejection; Alzheimer's disease; viral infections; fevers; psoriasis; arthritis; Sjogren's syndrome; Behcet's disease; Parkinson's disease; or glomerulonephritis.

16. The method according to claim 15, wherein the lung disorders and lung conditions comprise asthma, noneosinophilic asthma, non-specific airway hyper-responsiveness, chronic pulmonary obstructive disease, nosocomial pneumonia, endotoxemia-induced acute respiratory distress syndrome or related conditions.

* * * * *